United States Patent
Lampropoulos et al.

[11] Patent Number: 5,921,968
[45] Date of Patent: Jul. 13, 1999

[54] VALVE APPARATUS WITH ADJUSTABLE QUICK-RELEASE MECHANISM

[75] Inventors: Fred P. Lampropoulos, Pleasant Grove; Brian W. Stevens, Sandy, both of Utah

[73] Assignee: Merit Medical Systems, Inc., South Jordan, Utah

[21] Appl. No.: 08/978,492

[22] Filed: Nov. 25, 1997

[51] Int. Cl.[6] .................................................. A61M 5/00
[52] U.S. Cl. ........................ 604/246; 604/30; 604/167; 604/523
[58] Field of Search .................................. 604/246, 247, 604/249, 240, 248, 30, 31, 32, 256, 164, 167, 523, 537, 539

[56] References Cited

U.S. PATENT DOCUMENTS

| | | | |
|---|---|---|---|
| 4,723,550 | 2/1988 | Bales et al. | 128/334 |
| 4,857,062 | 8/1989 | Russell | 604/256 |
| 4,925,450 | 5/1990 | Imonti et al. | 604/240 |
| 4,978,341 | 12/1990 | Niederhauser | 604/167 |
| 5,059,186 | 10/1991 | Yamamoto et al. | 604/280 |
| 5,078,688 | 1/1992 | Lobodzinski et al. | 604/164 |
| 5,135,492 | 8/1992 | Melker et al. | 604/53 |
| 5,195,980 | 3/1993 | Catlin | 604/167 |
| 5,203,774 | 4/1993 | Gilson et al. | 604/165 |
| 5,224,929 | 7/1993 | Remiszewski | 604/30 |
| 5,269,764 | 12/1993 | Vetter et al. | 604/167 |
| 5,269,771 | 12/1993 | Thomas et al. | 604/213 |
| 5,273,546 | 12/1993 | McLaughlin et al. | 604/167 |
| 5,324,271 | 6/1994 | Abiuso et al. | 604/167 |
| 5,338,313 | 8/1994 | Mollenauer et al. | 604/249 |
| 5,350,364 | 9/1994 | Stephens et al. | 604/167 |
| 5,356,394 | 10/1994 | Farley et al. | 604/256 |
| 5,364,371 | 11/1994 | Kaman | 604/251 |
| 5,382,230 | 1/1995 | Bonn | 604/32 |
| 5,395,349 | 3/1995 | Quiachon et al. | 604/248 |
| 5,460,615 | 10/1995 | Storz | 604/167 |
| 5,514,109 | 5/1996 | Mollenauer et al. | 604/249 |
| 5,542,933 | 8/1996 | Marks | 604/188 |
| 5,575,767 | 11/1996 | Stevens | 604/53 |
| 5,584,314 | 12/1996 | Bron | 137/239 |
| 5,591,137 | 1/1997 | Stevens | 604/256 |
| 5,599,327 | 2/1997 | Sugahara et al. | 604/283 |

*Primary Examiner*—John D. Yasko
*Attorney, Agent, or Firm*—Workman, Nydegger, Seeley

[57] ABSTRACT

A hemostasis valve having an adjustable quick-release mechanism the hemostasis valve includes a tubular body having a lumen therethrough and a compression chamber formed in one end that communicates with the lumen. A resilient compressible seal having a longitudinal passageway aligned with the lumen is disposed within the compression chamber. The compressible seal includes a raised annular portion projecting into the passageway. The compressible seal is configured to selectively seal and unseal the lumen in response to a compressive force exerted on said compressible seal by a plunger. Changing the compressive force exerted by the plunger on the seal allows for selectively and progressively reducing the size of an opening provided by the raised annular portion in the passageway. A quick-release mechanism, comprising a quick-release lever and a quick release assembly, is movably attached to the tubular body and communicates with the plunger. The quick-release mechanism allows the compressible seal to selectively be in a compressible position or in a released position. A spring tends to urge the plunger and seal into a compressed position. However, a rotatable end cap is operably interconnected between the quick-release mechanism and the plunger for progressively adjusting the amount of compression force exerted by the plunger onto the seal in order to selectively compress or release the compressible seal.

33 Claims, 9 Drawing Sheets

VALVE APPARATUS WITH ADJUSTABLE QUICK-RELEASE MECHANISM

BACKGROUND OF THE INVENTION

1. The Field of the Invention

The present invention relates to valves, and, in particular, relates to hemostasis valves. More particularly, the invention relates to an adjustable hemostasis valve having a quick-release mechanism.

2. Relevant Technology

Several current surgical procedures require temporary and often repeated introduction of catheters and/or guidewires into the cardiovascular system of a patient. For example, using only a relatively small incision, a catheter can be introduced into the body of a patient and used to deliver fluid, such as medication, directly to a predetermined location within the cardiovascular system. Catheters can also be used for exploratory surgery and for removing tissue samples within a body. One increasingly common use for catheters is in the placement of small balloons which can be selectively inflated within a blood vessel. The balloons are used for opening blood vessels that have been blocked or partially blocked by plaque build-up. This opening or altering of the vein is referred to as angioplasty.

A common catheter design used in performing many of the procedures includes an elongated, flexible, cylindrical catheter body having a fluid flow passageway or a lumen extending along the interior of that catheter body. During one type of use, an end of the catheter is inserted into the body of the patient through an incision in a blood vessel in the cardiovascular system. The catheter is advanced along the internal passageway of the vessel until the end of the catheter is located at a desired predetermined location for conducting and intended activity.

A guidewire is a long, cylindrical, flexible wire that is commonly used for directing the catheter to the desired location within the body. A guidewire is typically smaller in diameter and more rigid than a catheter. It is, therefore, easier for a surgeon to first direct and advance a catheter within the cardiovascular system to the desired location within the body of the patient. The opposing end of the guidewire, positioned outside the body of the patient, is then received within the lumen of the catheter. Using the guidewire as a guide, the catheter is advanced along the length of the guidewire so as to properly position the catheter within the body of the patient. If desired, the guidewire can then be removed from within the catheter to open the lumen of the catheter. In an alternative process for inserting the catheter, the guidewire is initially received within the lumen of the catheter and the catheter and guidewire are simultaneously advanced within the cardiovascular system of the patient.

Operations using catheters can often require the insertion and removal of several different types of catheters and guidewires. One of the problems encountered with the insertion and removal of catheters and guidewires is controlling bleeding at the point where the catheters and guidewires are first introduced into the cardiovascular system.

In one approach to controlling bleeding and insuring easy insertion and removal of the catheter and/or guidewire within the cardiovascular system, one end of an introducer is first secured within a large vein of a patient. An introducer is a relatively large, hollow tube. The opposite end of the introducer is positioned outside the body of the patient and is attached to an adapter.

An adapter typically comprises a short, rigid tube having a passageway extending therethrough. Attached at one end of the adapter tube is a connector. The connector is used to connect the passageway of the adapter to the exposed end of the introducer. This enables fluids and/or medical instruments, such as catheters and guidewires, to pass between the adapter and the introducer.

Positioned at the opposite end of the adapter tube is a valve commonly referred to as a valve apparatus. The valve apparatus includes an enlarged chamber portion at the end of the adapter remote from the patient. The chamber is aligned with and is connected to the passageway extending through the adapter. Positioned within the chamber is some type of seal. During use of the adapter, the pressure of the blood causes blood from the patient to flow up through the introducer and into the passageway of the adapter tube. The seal, which either closes independently or is compressed around the catheter or guidewire, restricts blood from spilling out of the adapter through the access of the valve.

Various seal arrangements are available with different types of valve apparatus ranging from one seal to a plurality of seals. One of the main purposes of the valve arrangement is to be able to block off the passageway to stop the loss of bodily fluids from the valve apparatus. One type of seal that has been used in valve apparatus is a soft, cylindrical, compressible seal. The compressible seal has a passageway extending along the length of the seal. The seal is oriented in the chamber so that the passageway in the seal is aligned with and connected to the passage in the adapter tube.

To seal the valve apparatus that incorporates a compressible seal, a portion of the valve apparatus is advanced, typically a shaft, which in turn compresses the seal within the chamber. Compression of the seal causes the passageway in the compressible seal to constrict. If the shaft is advanced sufficiently far within the chamber, the passageway in the seal constricts so as to form a seal around the exterior surface of the catheter or guidewire positioned in the passageway. Alternatively, if the catheter or guidewire is removed from within the seal, the passageway in the seal can constrict in response to compression force so that the seal completely closes off the access through the valve.

Current designs that utilize compressible seals require the compressive force to be removed from the compressive seal in order to remove the catheter or guidewire from the valve apparatus. Removing the compression force often required rotating the end portion of the valve apparatus or some other way of incrementally removing the force. The present methods of removing the force take some amount of time which results in a needless loss of blood and increases the risk of contamination of the blood of the patient. It is important to be able to quickly make adjustments or insert/remove the guidewire or catheter without unnecessary time passing. Furthermore, leaking bodily fluids, including blood, may produce both a messy and slippery work environment for the surgeons. With the increasing number of blood disorders such as AIDS, blood leakage from the adapter increases the risk to the surgeon and other medical personnel.

Attempts have been made to solve the leakage problem by making valve apparatus that utilize two or more seals. Typical seals include duck-bill valves and slit valves. While multiple seals in the valve apparatus are useful in helping to reduce the loss of body fluids, including blood, several problems still exist. Current valve apparatus, regardless of whether the valve has one or two seals, generally have an open position and a closed or sealed position. Once the valve apparatus is closed, the surgeon is not able to move or reposition the catheter or guidewire without putting the valve apparatus into the open position where body fluids can flow out the valve. For example, if the valve utilizes a compressible seal, the catheter or guidewire cannot be repositioned or removed unless substantially all of the compressive force is removed from the compressible seal. Once the compression force is removed, the valve apparatus is no longer sealed. The available valve apparatus are not configured to provide a seal against a loss of bodily fluids while still allowing the catheter or guidewire within the valve to be repositioned.

An additional problem with existing valve apparatus is that the seals, and in particular those seals that are compressed to form a seal, tend to exert a force upon the catheter or guidewire. The forces, including the frictional forces acting on the instrument, are commonly referred to as "drag." The drag acting on the catheter or guidewire disposed in a seal makes it difficult for the surgeon to be able to adjust the catheter or guidewire. In particular, it is very difficult to be able to adjust the catheter or guidewire by the "feel" of the movement. Currently, the valve apparatus must be adjusted to remove the compression forces acting on the seal. Removing the compression forces acting on the seal results in fluid leakage.

Finally, having to remove the compression force, reposition or remove the catheter or guidewire, and then readjust the valve apparatus to compress the seal so as to form a seal is time consuming and in turn unnecessarily lengthens the procedure.

It will be desirable to have a valve apparatus that can be quickly opened and closed to reposition or remove a catheter or guidewire without having to remove the compression forces and is able to minimize blood leakage from the valve apparatus, or reset the desired amount of drag acting upon the guidewire or catheter. It would also be advantageous to have a valve apparatus in which the seal will remain sealed but will allow an instrument such as a catheter or guidewire to be longitudinally repositioned without exerting so much drag on the catheter or the guidewire that the surgeon is unable to have a feel for the movement of the guidewire or catheter.

SUMMARY AND OBJECTS OF THE INVENTION

It is therefore an object of the present invention to provide a valve apparatus that can be quickly unsealed and resealed to minimize the loss of body fluids while repositioning or removing medical instruments from the valve apparatus.

It is another object of the present invention to provide a valve apparatus that can be unsealed and resealed in a simple motion.

It is another object of the present invention to provide a valve apparatus that can be adjusted to have a desired seal, then quickly unsealed and resealed such that upon being resealed the valve apparatus will return to have substantially the same seal as before the valve apparatus was unsealed.

It is another object of the present invention to provide a valve apparatus that is capable of being sealed to prevent the loss of body fluids while still allowing longitudinal movement of the catheter or guidewire disposed in the valve apparatus.

In particular, it is an object of the present invention to provide a valve apparatus that includes a compressible seal which allows the valve apparatus to be sealed while still allowing the catheter or guidewire be longitudinally repositioned without having to completely remove the compressive forces acting on the seal.

It is yet another object of the present invention to provide a valve apparatus in which the mechanical forces acting on the catheter or guidewire while the catheter or guidewire is being repositioned can be selectively reduced or increased while a seal is maintained within a sealing window.

Still another object of the present invention is to provide a valve apparatus that allows the repositioning or removal of the catheter or guidewire with increased speed and substantially without the loss of body fluids.

Yet another object is to provide a valve apparatus which incorporates a compressible seal but enables a surgeon to move or reposition a catheter or seal by "feel" while still maintaining a sealed configuration in the valve.

Additional objects and advantages of the invention will be set forth in the description which follows, and in part will be obvious from the description, or may be learned by the practice of the invention. The objects and advantages of the invention may be realized and obtained by means of the instruments and combinations particularly pointed out in the appended claims.

To achieve the foregoing objects, and in accordance with the invention as embodied and broadly described herein, a hemostasis valve is provided that has a quick-release mechanism and an improved valve assembly that minimizes the loss of body fluids during repositioning or removing of medical instruments, such as catheters and guidewires, from the valve apparatus. The valve assembly includes a compressible seal that responds to compressive forces exerted thereon to seal the hemostasis valve. When compressive forces are progressively exerted on the compressible seal, a portion of the seal moves radially inward to form a progressively tighter seal around a catheter or guidewire that is disposed within the compressive seal. The amount of compressive force exerted on the compressible seal can be incrementally adjusted so that a seal is formed or maintained around the catheter or guidewire while still allowing the catheter or guidewire to be longitudinally repositioned or removed without having to remove substantially all of the compressive forces acting on the compressible seal.

In addition, the quick-release mechanism enables the valve apparatus to be completely opened and closed in a single, or relatively simple, movement for even quicker adjustments of the catheter or guidewire disposed therein. The quick-release mechanism can be selectively moved between an activated position and an inactivated position. When the quick-release mechanism is in the inactivated position, the valve assembly can be incrementally opened or closed depending on the amount of force acting on the compressible seal. When the quick-release mechanism is moved to the activated position, some or all of the compressive force is removed from the compressible seal, depending on the embodiment. Upon returning the quick-release mechanism back to the inactivated position, the compressible seal will return to substantially the same position with substantially the same amount or tightness of seal as before the quick-release mechanism was activated. The compressive forces acting on the compressible seal do not have to be removed or even adjusted prior to or after using the quick-release mechanism, since the original adjustment will be restored upon deactivating the quick-release mechanism.

In particular, the valve apparatus comprises a tubular body, a compressible seal, and a quick-release mechanism. The tubular body is generally elongated and has a lumen formed therethrough which is adapted for accessing the cardiovascular or other intravenous system of a patient. The tubular body has a distal end, a proximal end, and a compression chamber located at the proximal end thereof that is in communication with the lumen. The resilient compressible seal comprises sealing means and is disposed within the compression chamber and has a longitudinal passageway formed therethrough that is aligned with the lumen in the tubular body. The passageway in the compressible seal has a raised annular portion projecting into the passageway configured to selectively provide an opening to the lumen in the tubular body. The compressible seal is configured to selectively seal and unseal the lumen in response to a compressive force exerted on said compressible seal by selectively and progressively reducing the size of the opening provided by the raised annular portion in the passageway.

The valve apparatus also includes a quick-release mechanism and a biasing means. The quick-release mechanism comprises a lever hingedly attached to the tubular body and a quick-release assembly movably attached to the tubular body. The quick-release mechanism is selectively movable between an inactivated position in which the compressible seal is in a compressible position and an activated position in which the compressible seal is in a released position. In other words, "activating" the quick-release mechanism causes the valve to be in a released and substantially noncompressible state. The lever is selectively moved between an extended position in which the quick-release mechanism is in the inactivated position and an unextended position in which the quick-release mechanism is in the activated position. The quick-release mechanism is operably connected to the lever and is configured to move the compressible seal between the compressible position and the released position in response to the lever being selectively moved in a hinged movement toward or away from the tubular body.

The biasing means is mounted on said tubular body for urging the compressible seal into the compressible position in the compression chamber, and generally includes a spring communicating with a plunger which, in turn, can be adjusted to apply a desired amount of compressive force onto the compressible seal.

The valve apparatus also includes a rotatable end cap operably interconnected between the quick-release mechanism and the plunger for selectively adjusting and fine tuning the amount of compressive force applied to the compressible seal by the plunger. The end cap includes a shaft that is integrally formed therewith and which projects from the end cap. The shaft includes threads that engage corresponding threads within the plunger for threadably engaging the end cap and plunger such that the shaft is advanced or withdrawn within the compression chamber by rotation of the end cap. The rotatable end cap and plunger comprise a compressing mechanism that provide means for applying a desired compressive force onto the compressible seal. The biasing means may be considered to form part of the compressing means in some circumstances.

The quick-release mechanism is configured to overcome the opposing force of the biasing means in order to at least partially release the compressive force applied by the compressing means onto the sealing means. Thus, once the end cap has been rotated to a desired position to apply a desired compressive force and thereby form a desired seal, the quick-release mechanism allows the user to release the seal and then restore the desired seal in a simple motion. This allows the user to release and then restore the desired seal without having to readjust the end cap once the end cap has been rotated to a desired position in order to form a desired seal.

It would also be within the scope of the present invention to provide compressing means that applied a pre-set or predetermined level of compressive force to the sealing means such that the seal was preadjusted to a predetermined hole size and/or tightness such that the compressing means would not be adjustable. That way, the quick-release means would be used to open and then close, or unseal and then seal, the valve apparatus when desired to insert or adjust a catheter, guidewire, or other elongate device disposed within the valve apparatus.

These and other objects and features of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION OF THE PREFERRED EMBODIMENTS

Figure 1:
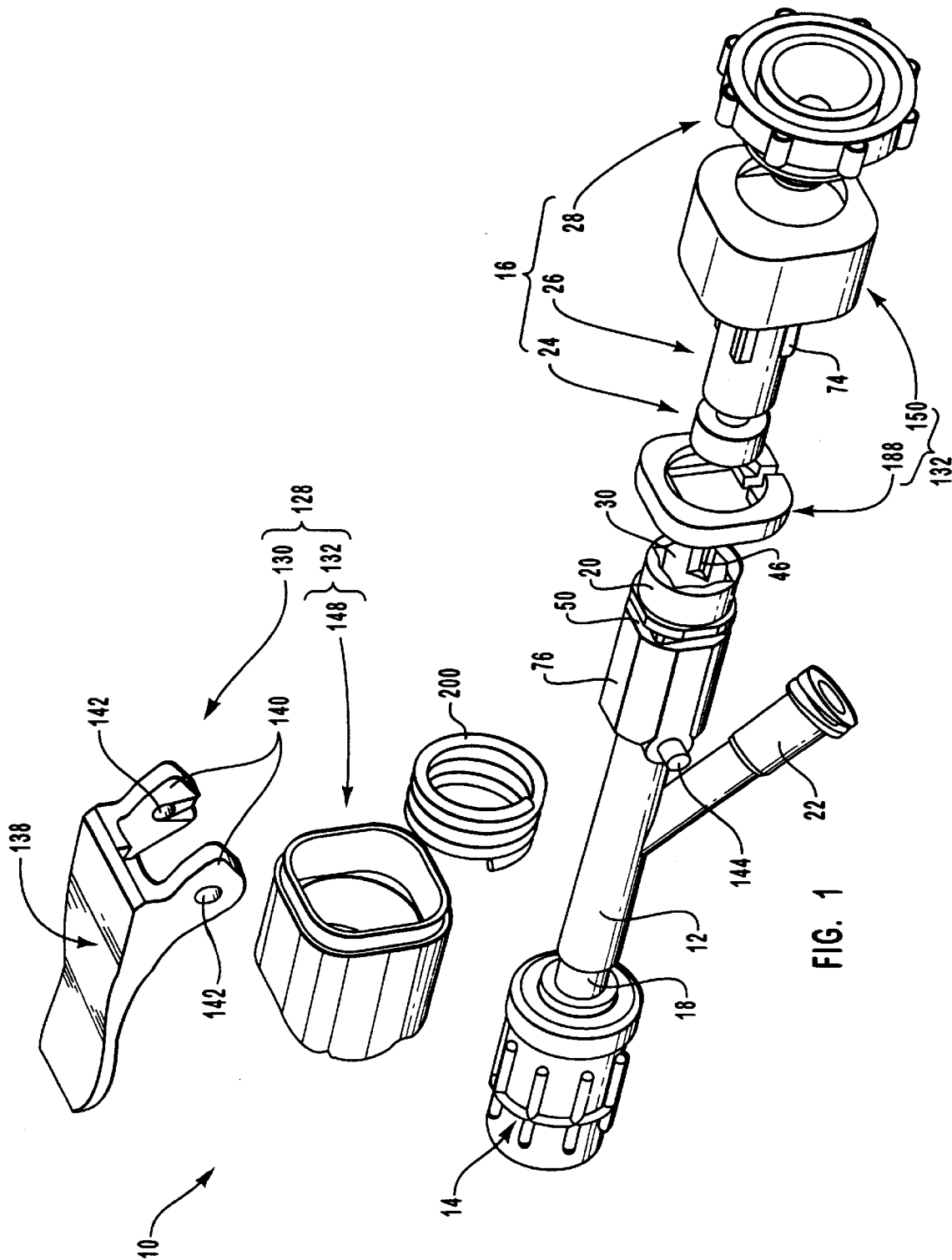
FIG. 1 is an enlarged perspective view of a valve apparatus according to the present invention including a compressing mechanism, a quick-release mechanism, and a valve assembly in a partially disassembled condition.

The present invention is an adjustable quick-release valve apparatus with a valve assembly that minimizes the loss of body fluids during repositioning or removal of medical instruments, such as catheters and guidewires, from the valve apparatus. The quick-release valve apparatus includes a valve assembly and a quick-release mechanism. The valve assembly includes a compressible seal that responds to compressive forces exerted thereon to seal the hemostasis valve. When compression force is exerted on the compressible seal, at least a portion of the seal moves radially inward to form a progressively tighter seal around a catheter or guidewire that is disposed in the compressive seal, or it can seal by itself. The amount of compressive force exerted on the compressible seal can be incrementally adjusted so that a seal is formed or maintained around the catheter or guidewire, while still allowing the catheter or guidewire to be longitudinally repositioned or removed without having to remove substantially all of the compressive forces acting on the compressible seal.

In addition, the quick-release mechanism enables the seal of the valve apparatus to be released and then substantially restored in a single movement for immediate unsealing and resealing of the valve without disturbing the aforementioned adjustment to the seal. The quick-release mechanism can be selectively moved between an activated position and an inactivated position. When the quick-release mechanism is in the inactivated position, the valve assembly may be selectively sealed or unsealed as desired by increasing or decreasing the amount of force acting on the compressible seal by the compressing means. If the quick-release mechanism is moved to the activated position, at lest a portion, and preferably all, of the compressive force is removed from the compressible seal. This allows the user to insert, remove or adjust the position of an instrument disposed therein without having to change the setting of the compressing means. Upon moving the quick-release mechanism back to the inactivated position, the compressible seal returns to substantially the same adjustment position with substantially the same compressive forces acting thereon as before activating the quick-release mechanism. Thus, the quick-release mechanism allows for immediate unsealing and resealing of the sealing means without altering the adjustment of the compressing means.

In order to assist in understanding the meaning and scope of certain terms, the following definitions are given. It should be understood that the following definitions are intended to clarify rather than completely replace the ordinary means of the terms.

The terms "seal" and "sealing", as used in the specification and the appended claims, shall refer to the act or process of increasing the compressive force acting on the sealing means such that the sealing means (e.g., compressive seal) tends to constrict. Conversely, the terms "unseal" and "unsealing", as used in the specification and the appended claims, shall refer to the act or process of decreasing the compressive force acting on the sealing means such that the sealing means tends to dilate. Whether or not the sealing means actually constricts or dilates due to changes in the compressive force acting thereon may depend on the existence or size of an elongated medical device disposed within the valve apparatus and the size of the "sealing window" of the particular sealing means being used. Thus, it is possible to increase or decrease the "seal" of the valve apparatus while maintaining a substantially constant opening through the sealing means.

The term "sealing window", as used in the specification and the appended claims, shall refer to the ability of the sealing means to maintain a level or tightness of sealing while allowing for a range of varying levels of compressive force applied to the sealing means, which in turn alters the sealing force or tightness of the sealing means around a medical device residing within the value apparatus. At the lower end of the sealing window, a level of sealing can be maintained while still facilitating longitudinal movement of the medical device through the valve apparatus. Outside the sealing window, increases or decreases in the compressive force acting on the sealing means will generally tend to respectively constrict or dilate the opening through the sealing means. Thus, the "sealing window" constitutes a range of varying tightness which facilitates longitudinal movement while yet maintaining a substantially leak-proof seal.

The term "release", as used in the specification and the appended claims, when used in conjunction with the quick-release means and compressing means in releasing or reducing the compressive force acting on the sealing means, shall refer to the tendency of the quick-release means to release or relax the compressive force acting on the sealing means. Although the quick-release means of the present invention is preferably configured to release substantially all the compressive force acting on the sealing means, it is within the scope of the present invention to provide a quick-release means which only releases a portion of the compressive force acting on the sealing means as long as the quick-release mechanism, when activated, facilitates or otherwise allows for easier longitudinal adjustment of an elongated medical device residing within the valve apparatus.

The term "restore", as used in the specification and the appended claims, when used in conjunction with the quick-release means and compressing means in reference to the restoration of the compressive force acting on the sealing means, shall refer to the tendency of the quick-release means to restore the same level or amount of compressive force applied to the sealing means when the quick-release means is deactivated as before the quick-release means was activated to release or reduce the compressive force applied to the sealing means. Thus, upon setting or adjusting the compressing means to attain a desired seal strength or tightness, the user need not significantly readjust the compressing means after activation and deactivation of the quick-release means since the desired setting and attendant seal strength or tightness will be substantially "restored" upon deactivating the quick-release means.

The term "restore" shall not, however, be construed to mean that no adjustment to the compressing means will ever be necessary under any circumstances. For example, removal of an elongated medical device from the valve apparatus will typically necessitate readjustment of the compressing means to maintain a seal, even though deactivation of the quick-release means will substantially "restore" the compressing means to its original setting prior to activating the quick-release means. Similarly, swapping differently sized medical devices or altering the medical procedure to require a tighter seal may also necessitate readjustment of the compressing means to maintain an adequate seal. Nevertheless, use of the same, or same sized, medical apparatus within the valve apparatus will typically obviate the need to adjust the compressing means upon utilizing the quick-release means.

In order to illustrate the inventive concepts of the quick-release means, compressing means, sealing means, and other mechanical features and functions of the present invention, the following preferred embodiments are set forth by way of example, though not by limitation. Any structure that can provide the necessary functions in order to carry out the inventive features of the present invention should be considered to fall within the scope of the present invention.

FIG. 1 depicts a preferred embodiment of a valve apparatus 10 of the present invention, which comprises a tubular body 12, a rotatable connector 14, and a valve assembly 16. Tubular body 12 has a distal end 18 and an opposing proximal end 20. Rotatable connector 14 is positioned at distal end 18 of tubular body 12. Rotatable connector 14 provides fluid coupling between an introducer (not shown) and tubular body 12. Valve assembly 16 is positioned at proximal end 20 of tubular body 12.

In the embodiment depicted in FIG. 1, tubular body 12 includes a first supplemental access tube 22 attached thereto. First supplemental access tube 22 is preferably positioned at an angle relative to the longitudinal axis of tubular body 12 so as to project outwardly from tubular body 12 towards proximal end 20 of tubular body 12. First supplemental access tube 22 has a central bore formed therethrough so as to be in fluid communication with tubular body 12. In addition, first supplemental access tube 22 is configured to be placed in fluid communication with an elongated device, such as a catheter. First supplemental access tube 22 can be used to introduce fluids or medical devices into the body of a patient. As shown in FIG. 1, the remote end of first supplemental access tube 22 has threads formed thereon to accommodate a conventional Luer lock attachment. Various other types of attachment structure may perform the attaching function thereof equally effectively. It can be appreciated that tubular body 12 may have various other configurations that are equally effective in carrying out the intended function thereof.

Valve assembly 16 includes a compressible seal 24, a plunger 26, and a rotatable end cap 28. The configuration and interrelationships of these components are more clearly shown in FIG. 2, which depicts a cross-sectional exploded view of the valve assembly 16 in a partially disassembled condition.

Figure 2:
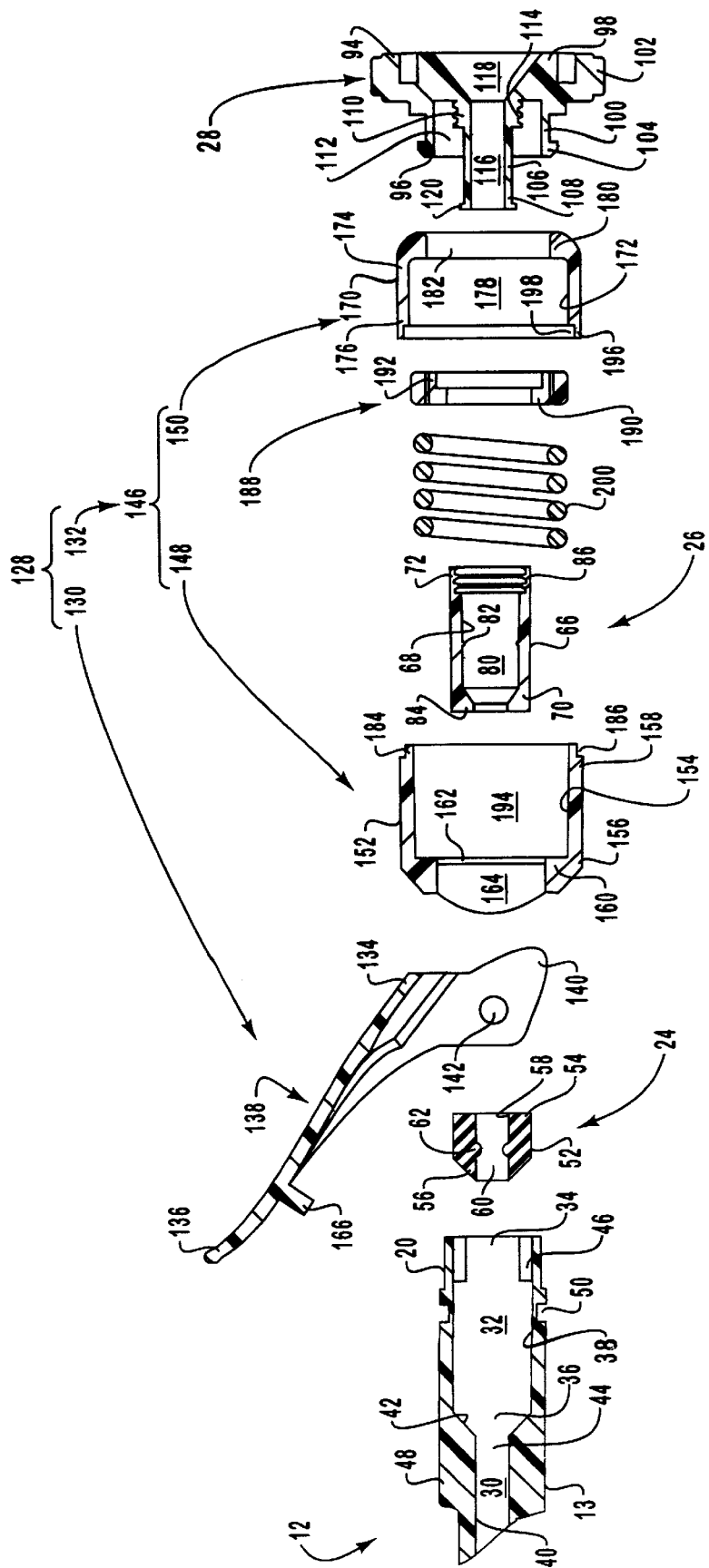
FIG. 2 is an enlarged cross-sectional view of a portion of the valve apparatus of FIG. 1 in a partially disassembled condition.

Tubular body 12 has a longitudinal passageway or lumen 30 extending through tubular body 12 as depicted in FIG. 2. At proximal end 20, tubular body 12 has a compression chamber 32 that is axially aligned with lumen 30. Compression chamber 32 has a proximal end 34 and a distal end 36. Compression chamber 32 is defined by an interior surface 38 that extends between proximal end 34 and distal end 36 thereof. Proximal end 44 of lumen 30 communicates with distal end 36 of compression chamber 32. Lumen 30 is preferably concentric with compression chamber 32 and has an interior surface 40 with a diameter smaller than the diameter formed by interior surface 38 of compression chamber 32. Lumen 30 is preferably substantially cylindrical in order to accommodate cylindrical medical devices.

Distal end 36 of compression chamber 32 preferably has a tapered shoulder 42 that extends from interior surface 38 of compression chamber 32 to interior surface 40 at proximal end 44 of lumen 30. The tapered shoulder 42 is configured to correspond to a compression seal 52, as discussed hereinafter. Interior surface 38 of compression chamber 32 transitions from being cylindrical at distal end 36 to being substantially square at proximal end 34 thereof (FIG. 1). At proximal end 34, compression chamber 32 has several recesses 46 formed therein as will be discussed in further detail below.

Tubular body 12 has an exterior surface 13 that is substantially cylindrical-shaped. Exterior surface 13 of tubular body 12 includes a substantially octagonal section 76 that surrounds compression chamber 30. Octagonal section 76 is configured to provide flat surfaces that enable medical personnel to clamp or use other mechanical means for holding valve apparatus 10. It can be appreciated that octagonal section 76 may have alternate embodiments including rectangular or hexagonal cross-sectional configurations that may be equally effective in performing the intended function thereof.

As depicted in FIGS. 1 and 2, exterior surface 13 of tubular body 12 also has a channel 50 formed in proximal end 20 of tubular body 12. Channel 50 will be discussed in further detail below. Tubular body 12 is one embodiment of structure capable of performing the function of a body means for providing lumen 30 therethrough which is adapted for accessing the cardiovascular or other intravenous system of a patient. It can be appreciated that various other embodiments of structure capable of performing the function of such a body means may be equally effective of carrying out the intended function thereof.

Valve assembly 16 comprises a resiliently deformable compressible seal 24. Compressible seal 24 is configured to be substantially the same size and shape as distal end 36 of compression chamber 32 so as to cooperate therewith. Compressible seal 24 has an exterior surface 52 extending between a proximal end 54 and a distal end 56. Exterior surface 52 of compressible seal 24 has a diameter approximately equal to the diameter defined by inner surface 38 at distal end 36 of compression chamber 32 such that compressible seal 24 can be received within compression chamber 32.

In one embodiment of compressible seal 24, depicted in FIGS. 1 and 2, exterior surface 52 of compressible seal 24 is substantially cylindrical in shape. In addition, distal end 56 of compressible seal 24 is tapered and is configured to cooperate with tapered shoulder 42 at distal end 36 of compression chamber 32. It can be appreciated that exterior surface 52 of compressible seal 24 may have other configurations so long as both compressible seal 24 and compression chamber 32 are configured to cooperate.

Compressible seal 24 has an interior surface 58 that defines a passageway 60 therethrough which extends longitudinally through compressible seal 24 and is axially aligned with lumen 30. In a preferred embodiment, a raised annular portion, such as by way of example and not limitation, raised annular rib 62 is integrally formed on interior surface 58 of compressible seal 24. As depicted in FIG. 2, raised annular rib 62 is semi-spherical in shape. It can be appreciated that the raised annular portion, such as raised annular rib 62, may have various other configurations and perform the functions thereof equally effectively. By way of example and not limitation, raised annular rib 62 may be shaped as half an ellipse, semi-circular, rectangular, half an octagon, square, or various other shapes, or it may be eliminated. The function and importance of raised annular rib 62 will be discussed in further detail below.

Compressible seal 24 preferably comprises a deformable, resilient material which allows compressible seal 24 to compress in response to a compressive force exerted on compressible seal 24 and either form a seal with itself (FIG.

Figure 7:
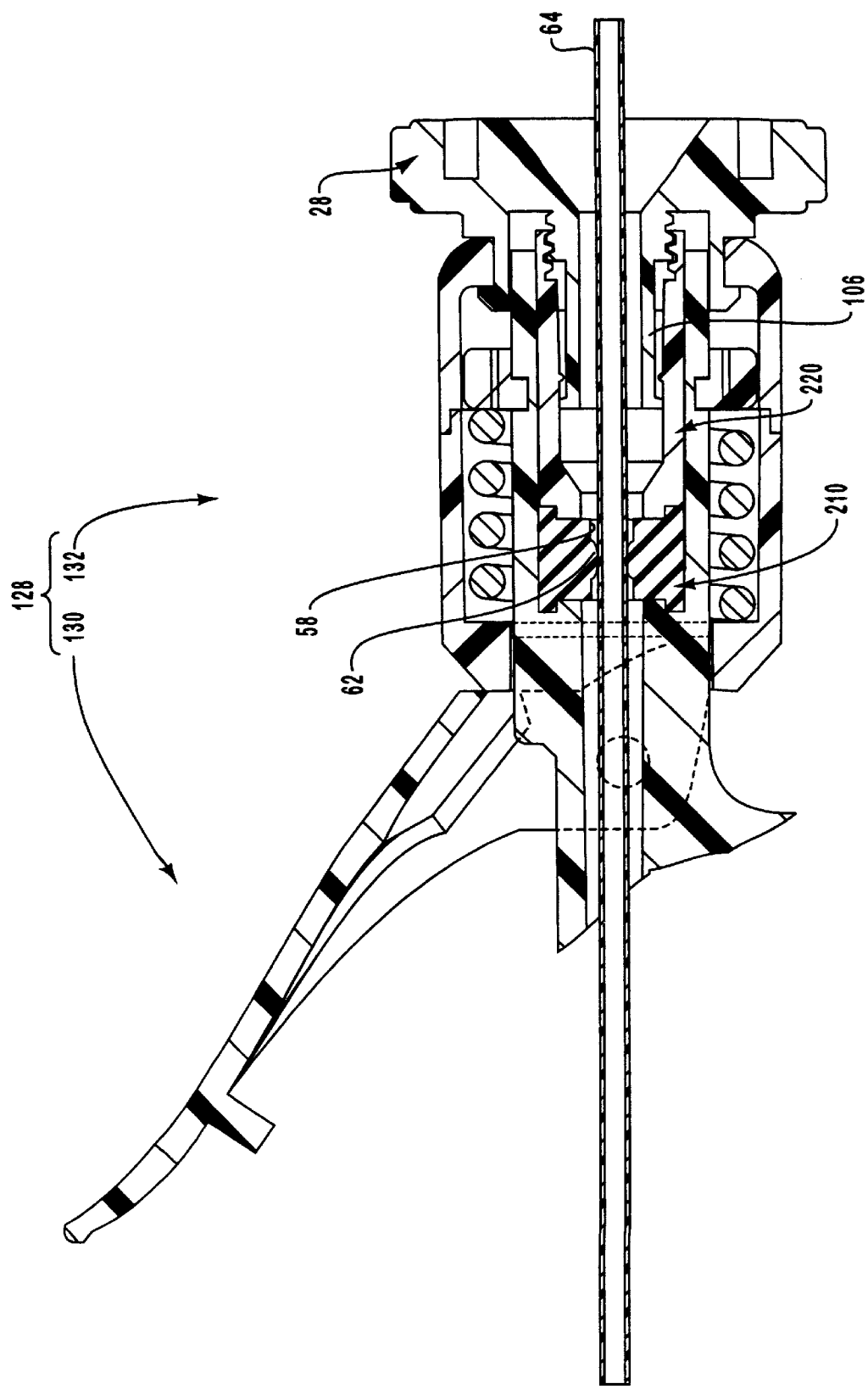
FIG. 7 is an enlarged cross-sectional view of the valve apparatus/elongated instrument combination of FIG. 6 with the quick-release mechanism in the inactivated position and the compressible seal in a sealed condition around the elongated instrument.

4) or form a seal around an elongated instrument 64 positioned through passageway 60 (FIG. 7). Compressible seal 24 is substantially composed of a material that is sufficiently resilient to enable compressible seal 24 to independently conform back to its original configuration when the compressive force is removed. The preferred material for compressible seal 24 is silicon rubber. It is, however, contemplated that compressible seal 24 may be substantially composed of other kinds of conventional rubbers and elastomeric materials.

Compressible seal 24 is one embodiment of a structure capable of performing the function of a sealing means for selectively sealing and unsealing lumen 30 in response to a compressive force exerted on the sealing means. The sealing means has a normally unsealed or open position when not subjected to compressive forces and responds to increasing compressive force by selectively and progressively reducing the size of passageway 60. The sealing means preferably includes a raised annular portion, such as raised annular rib 62, formed therein that is configured to allow elongated instrument 64 accessing lumen 30 through passageway 60 to be repositioned or removed while still maintaining a seal capable of preventing substantially all loss of body fluids beyond the sealing means without releasing substantially all the compressive force acting on the sealing means (FIG. 7). Other embodiments of structure capable of performing the function of such a sealing means may be equally effective in carrying out the intended function thereof.

Valve assembly 16 also includes plunger 26. As depicted in FIG. 2, one embodiment of plunger 26 is an elongated hollow member. Plunger 26 has an exterior surface 66 and an interior surface 68 extending between a distal end 70 and a proximal end 72. Exterior surface 66 of plunger 26 is sized and configured to cooperate with interior surface 38 of compression chamber 32 such that plunger 26 can be disposed in compression chamber 32. One embodiment of plunger 26, as depicted in FIGS. 1 and 2, has exterior surface 66 that is substantially cylindrical-shaped at distal end 70 and transitions to a substantially square proximal end 72. Plunger 26 may, however, be entirely cylindrical shaped and perform the function thereof equally effectively. Proximal end 72 has four ribs 74 that are sized and configured to be received in cooperating recesses 46 formed in interior surface 38 of compression chamber 32 (FIG. 1). The function of ribs 74 and recesses 46 is to prevent the twisting of plunger 26 as plunger 26 is advanced by rotating end cap 28 and shaft 106 in order to not cause twisting or rotation of seal 24 as it is being compressed or uncompressed. As shaft 106 rotates when end cap 28 is rotated, plunger 26 is selectively advanced or retracted relative to seal 24. It can be appreciated that exterior surface 66 of plunger 26 may have various other configurations as long as plunger 26 can be received in compression chamber 32.

Interior surface 68 of plunger 26 has a diameter configured to cooperate with rotatable end cap 28, as will be discussed in further detail below. Interior surface 68 defines a longitudinal bore 80 formed through plunger 26. Longitudinal bore 80 has a raised annular retaining ring 82 formed therein. Annular retaining ring 82 has a diameter smaller than the diameter of longitudinal bore 80 formed by interior surface 68. The function of annular retaining ring 82 will be discussed in further detail below. Interior surface 68 of longitudinal bore 80 at proximal end 72 of plunger 26 may have first engagement threads 86 formed therein which will be discussed in further detail below.

Distal end 70 of plunger 26 has a force transferring portion 84 formed on interior surface 68 of longitudinal bore 80, which abuts proximal end 54 of compressible seal 24. In one embodiment of plunger 26, as illustrated in FIGS. 1 and 2, force transferring portion 84 projects radially inward to reduce the diameter of longitudinal bore 80 at distal end 70 so that it is substantially the same size as passageway 60 of compressible seal 24. This makes the surface area of distal end 70 of plunger 26 in contact with proximal end 54 of seal 24 substantially the same in order to more evenly distribute the compressive forces being applied by plunger 26 to compressible seal 24. Various other embodiments of plunger 26 may be capable of performing the function thereof equally effectively. By way of example and not limitation, plunger 26 could have a substantially cylindrical configuration over the entire length thereof. What is required is that plunger 26 be similarly sized and configured as compression chamber 32 in proximal end 20 of tubular body 12 so as to be received therein. In addition, plunger 26 may communicate with compressible seal 24 in a different way and yet perform the function thereof equally effectively. What is required is that plunger 26 be able to transfer compressive forces to compressible seal 24.

Rotatable end cap 28, shown in FIGS. 1 and 2, is substantially cylindrical and has a proximal end 94 and an opposing distal end 96. End cap 28 comprises an end wall 98 on proximal end 94 thereof and a side wall 100 integrally formed with end wall 98. A plurality of gripping ribs 102 may be included which extend radially outward on the periphery of end cap 28 and are aligned with the longitudinal axis of tubular body 12. The diameter of end cap 28 is preferably large enough so that the peripheral edge can be grasped by the user without the finger of the user running into other parts of valve apparatus 10. The exterior surface of side wall 100 has a compression collar 104 formed thereon which extends radially outward from the exterior surface of side wall 100. The diameter of the interior surface of side wall 100 is substantially the same as the diameter of exterior surface 13 of proximal end 20 of tubular body 12.

Rotatable end cap 28 further includes a tubular shaft 106 that projects distally from end wall 98. Shaft 106 has a distal end 108 and a proximal end 110. An annular flange 120 projects radially outward from distal end 106. Annular flange 120 has an outer diameter that is substantially the same as the inner diameter of plunger 26 formed by interior surface 68. The outer diameter of annular flange 120 on distal end 108 of shaft 106 is, however, slightly larger that the diameter of raised annular retaining ring 82 formed in longitudinal bore 80 of plunger 26. The interaction of raised annular retaining ring 82 in plunger 26 and annular flange 120 on shaft 106 will be discussed in further detail below.

Shaft 106 and side wall 100 of end cap 28 define a recessed chamber 112 therebetween. At proximal end 110 of shaft 106, the exterior surface of shaft 106 has second engagement threads 114 formed therein. Second engagement threads 114 are configured to complementarily engage first engagement threads 86 on proximal end 72 of plunger 26 for rotational threaded engagement. The rotational threaded engagement between first engagement threads 86 and second engagement threads 114 causes plunger 26 to selectively advance or retract within compression chamber 32 against compressible seal 24 as end cap 28 is rotated. Plunger 26 and shaft 106 are one example of structure capable of performing the function of a shaft means for selectively applying compressive force on compressible seal 24.

First engagement threads 86 and second engagement threads 114 are one embodiment of structure capable of performing the function of a means for coupling shaft 106 to plunger 26 for selectively advancing plunger 26 into compression chamber 32 so as to compress compressible seal 24 disposed within compression chamber 32. Various other configurations of first engagement threads 86 and second engagement threads 114 may perform the function thereof equally effectively.

The present invention also envisions using all other comparable configurations or alternative types of coupling and advancing. By way of example and not limitation, first engagement threads 86 could be formed on exterior surface 66 of proximal end 72 of plunger 26 (not shown). Correspondingly, second engagement threads 114 would then be complementarily positioned on the interior surface of side wall 100 of end cap 28 (not shown). Alternatively, complimentary sets of barbs or ridges (not shown) could replace first engagement threads 86 and second engagement threads 114. As plunger 26 is advanced within compression chamber 32, the complimentary sets of barbs or ridges (not shown) could mechanically interact to couple shaft 106 to plunger 26.

Shaft 106 has an entry way 116 formed therethrough. Entry way 116 extends longitudinally through shaft 106 and end wall 98. Entry way 116 expands radially outward at proximal end 94 of end cap 28 to form an enlarged retaining mouth 118. Retaining mouth 118 is configured to assist in guiding elongated medical instruments, such as catheters and guidewires, into valve apparatus 10.

Rotatable end cap 28 and plunger 26 are one example of structure capable of performing the function of a compressing means for selectively increasing a compressive force on the sealing means when the compressing means is rotated in one direction relative to a body means and for selectively decreasing the compressive force on the sealing means when rotated in an opposite direction relative to the body means. Various embodiments of structure capable of performing the function of such a compressive means may be equally effective in carrying out the intended function thereof. By way of example and not limitation, shaft 26 could be lengthened so as to exert compressive forces on compressible seal 24 itself instead of plunger 26. In this embodiment, coupling means (not shown) would be formed between shaft 106 and tubular body 12 or housing 150.

It is also within the scope of the present invention to provide non-adjustable compressing means, such as compressing means set or adjusted at a predetermined amount of compressive force such that compressible seal 24, or other sealing means, would be pre-set to have a predetermined hole size and/or tightness. In such an embodiment the quick-release means, to be discussed hereinbelow, will preferably be used to open and then close, or unseal and then seal, the valve apparatus when desired to insert or adjust a catheter, guidewire, or other elongate device disposed within the valve apparatus.

Valve Apparatus 10 also includes a quick-release mechanism 128 movably attached to tubular body 12. Quick-release mechanism 128 is configured to selectively move between an inactivated position, which allows compressible seal 24 to be in a compressible position, and an activated position, which causes compressible seal 24 to be in a released position with substantially no compressive force acting on compressible seal 24. Quick-release mechanism 128 comprises a quick-release lever 130 hingedly attached to the tubular body 12 and a quick-release assembly 132 moveably attached to the tubular body 12 (FIGS. 1 and 2). It should be understood that it is also within the scope of the present invention to provide a quick-release mechanism configured to release only a portion of the compressive force acting on the sealing means by the compressing means so long as it significantly facilitates longitudinal adjustment of an elongated medical device disposed within value apparatus 10.

Quick-release lever 130 has a proximal end 134 and a distal end 136. Quick-release lever 130 comprises an elongated handle 138 and a pair of opposing ears 140 attached thereto as depicted in FIGS. 1 and 2. Distal end 136 of lever 130 is formed by one end of the handle 138. Handle 138 is substantially elongated and contoured to be easily grasped by the user of valve apparatus 10.

One embodiment of handle 138 has an optional end stop 166 that projects away from handle 138 toward tubular body 12. End stop 166 prevents lever 130 from being rotated so far toward tubular body 12 when moving lever 130 into the activated position that the fingers of the user are pinched between the tubular body 12 and handle 138. Opposing ears 140 are attached to each side of handle 138 at the proximal end 134 of the quick-release lever 130 SO as to extend away from handle 138 toward tubular body 12. Ears 140 have a spaced-apart relationship, as shown in FIG. 1, and extend beyond proximal end 134 of lever 130 in a direction toward the proximal end 20 of tubular body 12. Ears 140 are configured to act as a cam to move quick-release assembly 132, as will be discussed below. Various other configurations of quick-release lever 130 may be equally effective in performing the function thereof.

Ears 140 each have an aperture 142 formed therethrough configured to receive therein one of two corresponding pins 144 (FIG. 1) formed on either side of exterior surface 13 of tubular body 12. Although only one pin 144 is visible in FIG. 1, it is contemplated that a second pin 144 is formed on the side of tubular body 12 substantially opposite from pin 144. As a result, tubular body 12 has two pins 144 which extend outwardly from tubular body 12 in a direction that is substantially perpendicular to the longitudinal axis of tubular body 12. In FIGS. 1 and 2, pins 144 and apertures 142 are depicted as being substantially cylindrical in shape. Pins 144 and apertures 142 could, however, have other configurations. For example, instead of being a through-wall aperture, apertures 142 comprises recesses that do not extend all the way through ears 140. Similarly, pins 144 could be shaped half spheres that are received in either through-wall apertures or recesses in ears 140. There are many configurations of pins 144 and apertures 142 that may be capable of carrying out the intended function thereof equally effectively.

Quick-release lever 130 can be selectively rotated about pins 144 in a levered action between an extended first position with lever 130 extending laterally away from tubular body 12 and in which quick-release mechanism 128 is in the inactivated position and an unextended second position in which lever 130 is proximal to tubular body 12 and in which the quick-release mechanism 128 is in the activated position. Quick-release lever 130 can be selectively rotated toward tubular body 12 until end stop 166 contacts exterior surface 13 of tubular body 12. This places the quick-release mechanism 128 in the activated position such that compressible seal 24 is caused to be in a substantially released position.

As depicted in FIGS. 1 and 2, one embodiment of quick-release lever 130 is pivotally attached to tubular body 12 for rotational movement. Various other methods of movably mounting quick-release lever 130 may be equally effective. By way of example and not limitation, quick-release lever 130 could be slidably mounted on tubular body 12. Instead of rotational movement, quick-release lever 130 could slide longitudinally relative to tubular body 12 between a first position and a second position causing quick-release mechanism 128 to slide between the inactivated position and the activated position. This could be achieved by using pins, such as pins 144, that are disposed in longitudinal slots or recesses instead of apertures 142.

Figure 3:
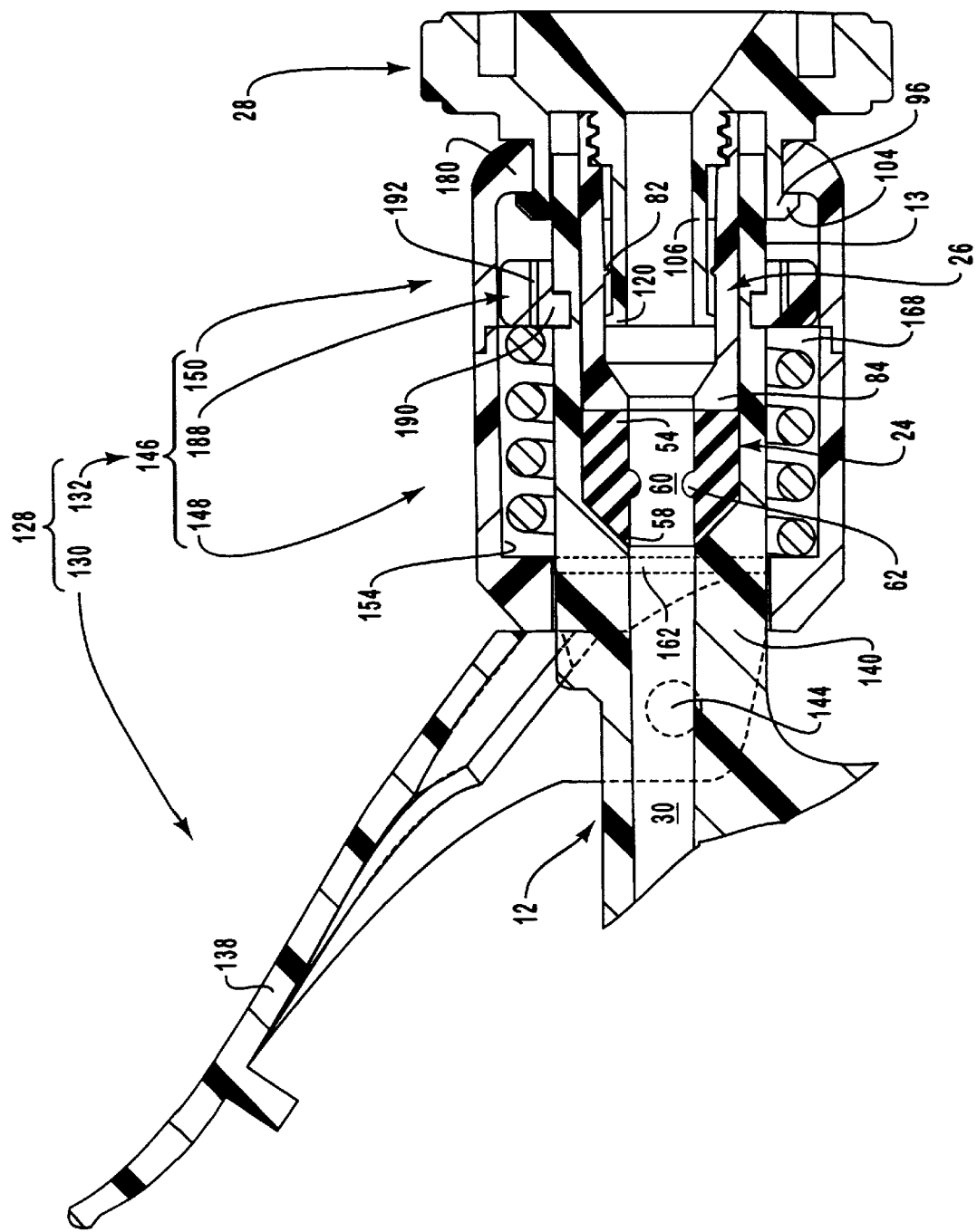
FIG. 3 is an enlarged cross-sectional view of a portion of the valve apparatus of FIG. 1 in an assembled condition showing the quick-release mechanism in an inactivated position and the compressible seal in an uncompressed, unsealed condition.

Quick-release assembly 132 includes a casing assembly 146, shown in FIGS. 2 and 3, that comprises a cover 148 and a housing 150. Casing assembly 146 is movably disposed around exterior surface 13 of tubular body 12. When disposed around tubular body 12, casing assembly 146 has a spaced-apart relationship with exterior surface 13 of body 12. The interior surface of casing assembly 146 and exterior surface 13 of tubular body 12 define a gap 168 therebetween (FIG. 3).

As depicted in FIG. 2, cover 148 is a hollow tubular member with an exterior surface 152 and an interior surface 154 that extend between a distal end 156 and a proximal end 158. Distal end 156 of cover 148 includes lips 160 and end walls 162. Lips 160 extend radially inward from interior surface 154, while end walls 162 extend between lips 160. End walls 162 are substantially perpendicular to the longitudinal axis of tubular body 12. An opening 164 is defined by lips 160 and end walls 162 and is smaller than the diameter formed by interior surface 154 of cover 148. Opening 164 is sized and configured so as to receive tubular body 12 therein. Opening 164 may have other configurations to perform the same function thereof as long as it is configured and sized so as to be able to cooperate with exterior surface 13 of tubular body 12.

Ears 140 of quick-release lever 130 push against end walls 162 when quick-release lever 130 is rotated between the extended first position and the unextended second position, thereby forcing quick-release assembly 132 to move longitudinally over tubular body 12 toward proximal end 20. This causes quick-release mechanism 128 to move from the inactivated position to the activated position.

An annular first tongue 184 projects longitudinally from proximal end 158 of cover 148. The outside diameter of first tongue 184 defines a first recess 186. First tongue 184 encircles opening 194 defined by interior surface 154 of cover 148. Exterior surface 152 of cover 148 may have a substantially rectangular configuration for providing a flat surface for medical personnel to, e.g., attach an appropriate tool thereto. It can be appreciated that the rectangular portion of cover 148 may have alternate embodiments, including octagonal or circular cross-sectional configurations, that may be equally effective in performing a desired function.

Housing 150 is hollow with an exterior surface 170 and an interior surface 172 that extend between proximal end 174 and distal end 176. Interior surface 172 defines an opening 178 configured to receive tubular body 12 therein. Distal end 176 of housing 150 has an annular second tongue 196 projecting distally therefrom. The interior diameter of second tongue 196 defines a second recess 198 configured to cooperate with first tongue 184 on proximal end 158 of cover 148. Once assembly of the internal sealing components has been accomplished, proximal end 158 of cover 148 and distal end 176 of housing 150 are fixedly attached using adhesives that are commonly used in the medical field. Other methods of attaching distal end 176 of housing 150 and proximal end 158 of cover 148 may be equally effective in performing the function thereof.

Proximal end 174 of housing 150 includes a retention collar 180 formed thereon that extends radially inward. Retention collar 180 defines an aperture 182 that is smaller than opening 178 defined by interior surface 172 of housing 150. Aperture 182 is smaller than the outer diameter of compression collar 104 formed on distal end 96 of side wall 100 of end cap 28. Compression collar 104 and retention collar 180 cooperate to retain end cap 28 within quick-release mechanism 128 in a rotatable engagement.

As depicted in FIGS. 1 and 2, valve apparatus 10 includes an optional clip 188 comprising a first ring 190 and a second ring 192. First ring 190 has an inner diameter that is smaller than the inner diameter of second ring 192. First ring 190 is sized and configured to cooperate with channel 50 in exterior surface 13 of tubular body 12. As shown is FIGS. 1 and 2, channel 50 and first ring 190 are substantially square to prevent rotation therebetween. Other configurations of channel 50 and first ring 190 may be equally effective in performing the function thereof as long as they are sized and configured to cooperate.

The inner diameter of second ring 192 is substantially the same as the diameter of exterior surface 13 of tubular body 12. As illustrated in FIG. 2, first ring 190 and second ring 192 are substantially square-shaped. Both first ring 190 and second ring 192 may have various other configurations and perform the function thereof equally effectively as long as the interior diameter of first ring 190 is configured to be received in channel 50 in exterior surface 13 of tubular body 12. The outer diameters of exterior surface of first ring 190 and second ring 192 are substantially the same. First ring 190 and second ring 192 may have different sizes and configurations than the embodiments illustrated, as long as both clip 188 and exterior surface 13 with channel 50 formed therein are similarly configured so as to secure clip 188 in place relative to tubular body 12. The function of clip 188 will be discussed in further detail relative to FIGS. 3–6.

Valve apparatus 10 includes quick-release means for selectively moving compressible seal 24 between a substantially released position, wherein the compressive force exerted by the compressing means onto the sealing means is substantially released or reduced, and a compressible position in which compressible seal 24 can be subject to a compressive force. One example of structure capable of performing the function of such quick-release means comprises quick-release mechanism 128.

Valve apparatus 10 also includes biasing means for urging compressible seal 24 into a compressed position, depending on the orientation of rotatable end cap 28. As such, the biasing means may properly be considered to be part of the compressing means in some cases since the biasing means urges the compressing means to apply a compressive force onto the sealing means. Because the quick-release mechanism is used to overcome the force of the biasing means, the biasing means urges the quick-release mechanism 128 into the inactivated position. One example of structure capable of performing the biasing function of such a biasing means comprises a spring 200. As depicted in FIGS. 1 and 2, spring 200 is preferably a helical spring, although other embodiments of spring 200 may be used which perform the function thereof substantially equally. By way of example and not limitation, spring 200 may comprise either a round-wire or a square-wire helical spring.

The coils of spring 200 have an inner diameter approximately equal to the diameter formed by exterior surface 13 of proximal end 20 of tubular body 12. Spring 200 is configured to cooperate with exterior surface 13 of proximal end 20 of tubular body 12. The exterior diameter of spring 200 is approximately the same as the diameter formed by the interior diameter of casing 146 which comprises housing 150 and cover 148. Consequently, the exterior diameter of spring 200 is approximately the same as the diameter of interior surface 154 of cover 148 and interior surface 172 of housing 150.

FIG. 3 depicts valve assembly 16 and quick-release mechanism 128 in an assembled condition. Quick-release mechanism 128 is movably mounted over tubular body 12. Specifically, quick-release lever 130 is mounted on pins 144. Pins 144 are disposed in apertures 142 formed in ears 140 of quick-release lever 130. Cover 148 is mounted on exterior surface 13 of tubular body 12. Interior surface 154 of cover 148 and exterior surface 13 of tubular body 12 have a spaced apart relationship and define a gap 168 therebetween. Spring 200 is disposed around exterior surface 13 of tubular body 12 within gap 168.

Clip 188 is mounted on proximal end 20 of body 12. As depicted in FIG. 3, first ring 190 of clip 188 is disposed in channel 50 formed in exterior surface 13 of tubular body 12. The inner diameter of second ring 192 of clip 188 abuts exterior surface 13. Clip 188 retains one end of spring 200 in place relative to tubular body 12.

Annular second tongue 196 extending distally from distal end 176 of housing 150 is disposed in first annular recess 186 (FIG. 2) formed in proximal end 158 of cover 148. Similarly, annular first tongue 148 that extends proximally from proximal end 158 of cover 148 is received in second annular recess 198 (FIG. 2) formed in distal end 174 of housing 150. The diameter of interior surface 172 of housing 150 is substantially the same as the diameter of interior surface 154 of cover 148 and the outer diameter of clip 188. Proximal end 174 of housing 150 is rotatably connected with distal end 96 of rotatable end cap 28.

In assembly, because the outer diameter of compression collar 104 is slightly larger than aperture 182 formed by retention collar 180 on proximal end 174 of housing 150, end cap 28 has to be forced past retention collar 180 in a snap-fit type engagement. Compression collar 104 on end cap 28 and retention collar 180 on housing 150 assist in keeping end cap 128 connected to housing 150 of quick-release mechanism 128. When end cap 28 is first attached to proximal end 174 of housing 150, retention collar 180 on proximal end 174 of housing 150 expands radially outward and/or side wall 100 is compressed radially inward as compression collar 104 passes through aperture 182 (FIG. 2) formed by retention collar 180. Once compression collar 104 passes beyond retention collar 180, retention collar 180 and/or side wall 100 return to their original configuration such that the abutment of compression collar 104 against proximal end 174 of housing 150 assists in retaining proximal end 96 of end cap 28 within housing 150, but allows for rotational movement of end cap 128.

Referring to FIGS. 2 and 3, it can be seen that compressible seal 24 is disposed in distal end 36 of compression chamber 32 (FIG. 2) when valve apparatus 10 is assembled. Plunger 26 is disposed in compression chamber 32 against compressible seal 24 (FIG. 2) such that force transferring portion 84 of distal end 36 of plunger 26 abuts proximal end 54 of compressible seal 24. As depicted in FIG. 3, force transferring portion 84 of distal end 36 of plunger 26 has substantially the same thickness as proximal end of compressible seal 24 so that the compressive force can be evenly transferred from plunger 26 to compressive seal 24.

Shaft 106 of rotatable end cap 28 is disposed in longitudinal bore 80 (FIG. 2) of plunger 26. Annular flange 120 has an outer diameter that is slightly larger than the inner diameter of annular retaining ring 82 to assist in retaining shaft 106 within bore 80 of plunger 26 once assembled. When shaft 106 is first disposed in longitudinal bore 80, annular retaining ring 82 and plunger 26 expand radially outward as annular flange 120 passes beyond annular retaining ring 82 through longitudinal bore 80. Once annular flange 120 is beyond annular retaining ring 82, plunger 26 returns to its original configuration, thus tending to lock shaft 106 within bore 80. Once past retaining ring 82, shaft 106 can move longitudinally within bore 80. Distal end 70 of plunger 28 is interconnected with proximal end 110 of shaft 106 by first engagement threads 86 of plunger 28 and second engagement threads 114 of end cap 28. First engagement threads 86 and second engagement threads 114 allow rotational movement of end cap 28 relative to plunger 26 and also cause plunger 26 to be selectively advanced or retracted within compression chamber 32 in order to incrementally alter the compressive force exerted by plunger 26 on compressible seal 24.

Quick-release mechanism 128 is selectively movable between an inactivated position in which compressible seal 24 is in a compressible position in compression chamber 32 and an activated position in which compressible seal 24 is in a substantially released position. Quick-release lever 130 is selectively rotatable between an extended first position and an unextended second position. Upon quick-release lever 130 being rotated away from tubular body 12 into the extended first position, as depicted in FIG. 3, quick-release assembly 132 is in the inactivated position which causes compressible seal 24 in 11 compression chamber 32 to be in a compressible position. The degree of sealing within compressible seal 24 can now be adjusted by selectively rotating end cap 28. The plunger 26 depicted in FIG. 3 is in its most withdrawn position such that it exerts little, if any, compressive force on compressible seal 24.

Figure 4:
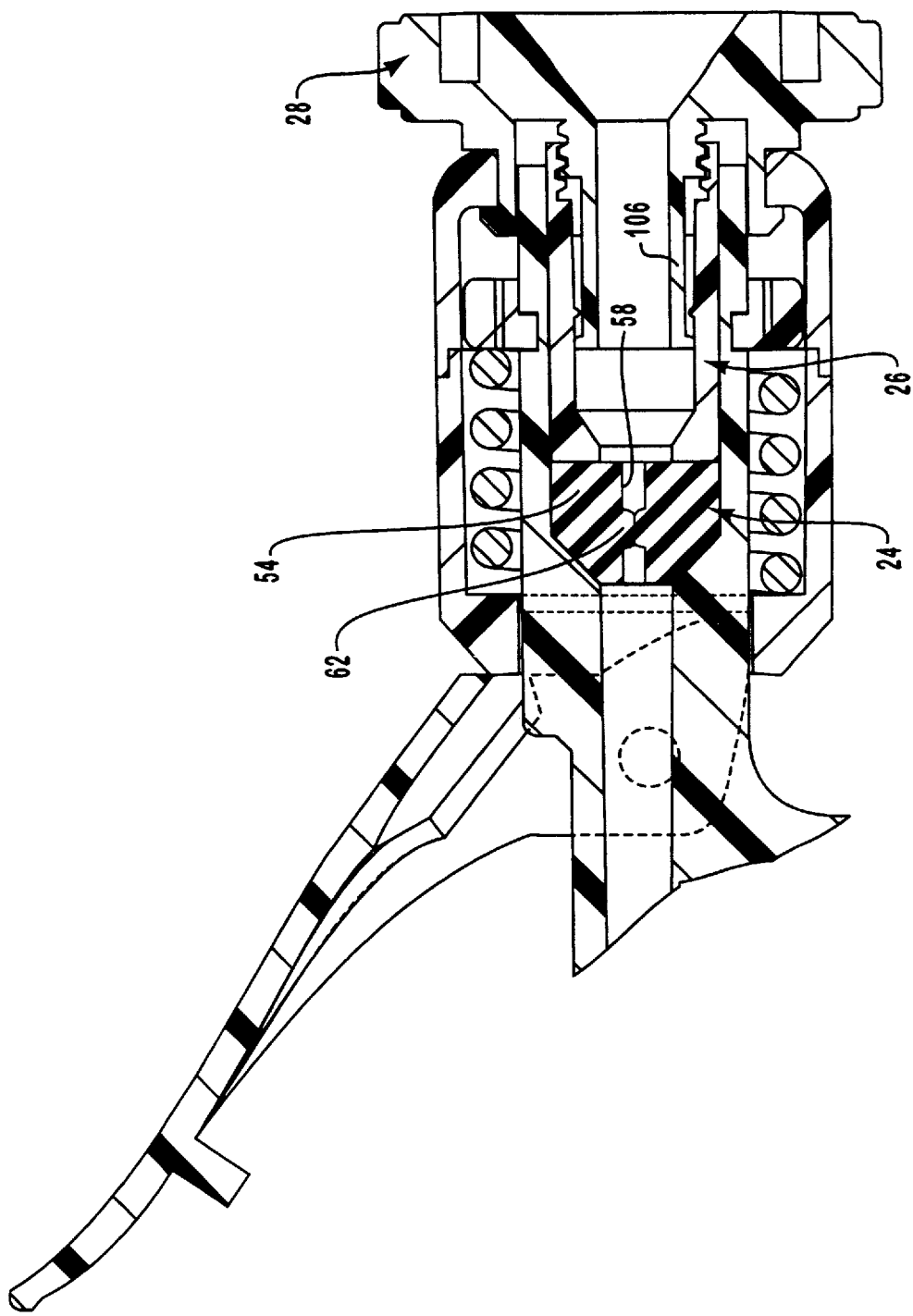
FIG. 4 is an enlarged cross-sectional view of the valve apparatus of FIG. 3 showing the quick-release mechanism in an inactivated position and the compressible seal in a sealed condition.

Compressible seal 24 can be completely closed off, as shown in FIG. 4, by selectively rotating end cap 28 to advance plunger 26 toward compressible seal 24. The advancement of plunger 26 exerts progressively increasing compressive force upon proximal end 54 of compressible seal 24. As plunger 26 advances, compressible seal 24 is progressively compressed, which in turn causes raised annular rib 62 and interior surface 58 of compressible seal 24 to project radially inward toward itself, thereby tending to constrict passageway 60. Simultaneously, compressible seal 24 compresses radially outward against interior surface 38 of compression chamber 32 (FIG. 2) so as to form a seal therebetween. Plunger 26 can continue to be advanced until passageway 60 is completely constricted as raised annular rib 62 is pressed together against itself to completely close and seal passageway 60, as depicted in FIG. 4.

Figure 5:
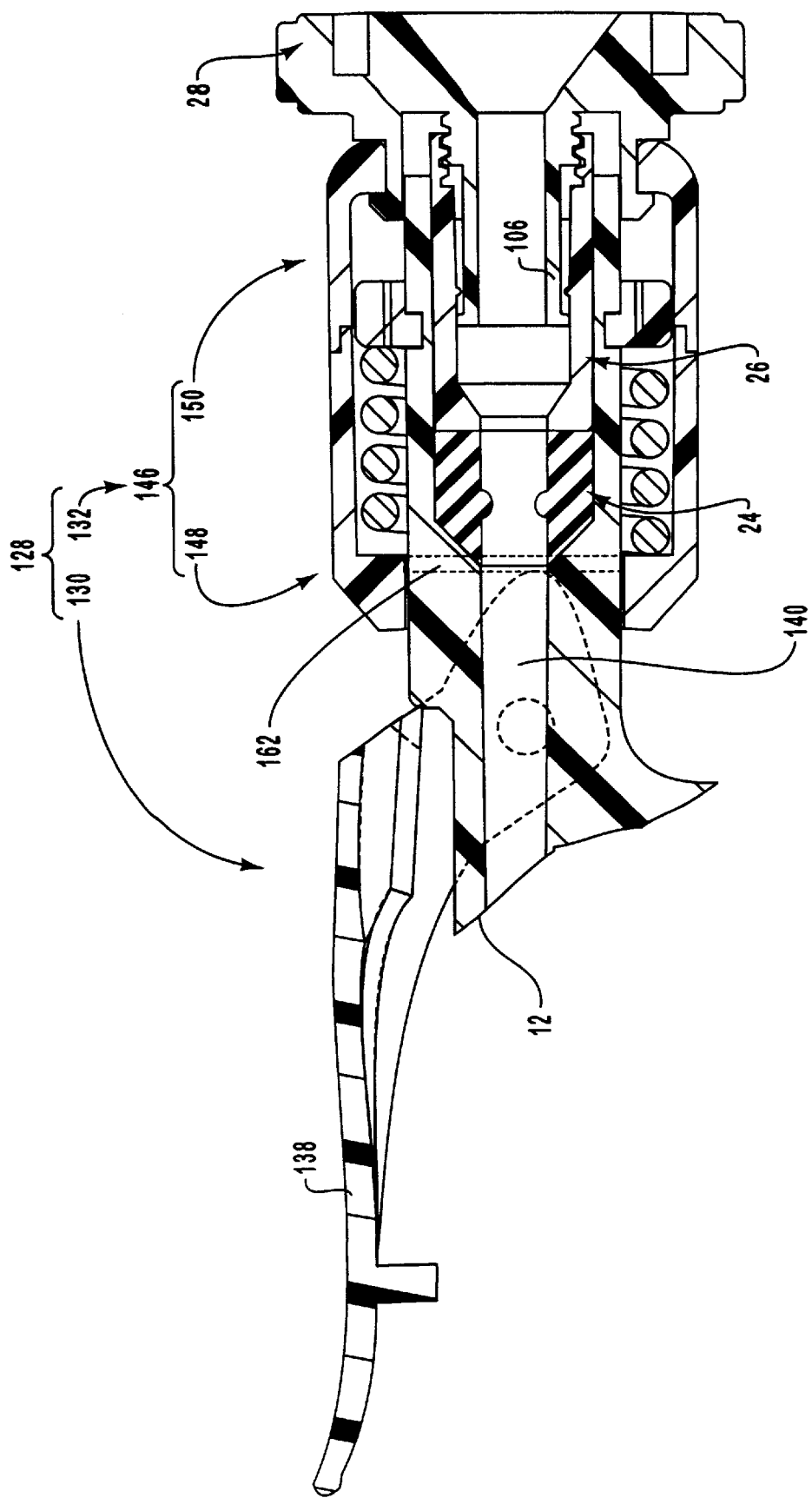
FIG. 5 is an enlarged cross-sectional view of the valve apparatus of FIG. 4 showing the quick-release in an activated position and the compressible seal moved into an uncompressed, unsealed condition.

As depicted in FIG. 5, quick-release mechanism 128 can be moved to the activated position in order to place compressible seal 24 in a released and open position. Specifically, quick-release lever 130 can be been rotated toward tubular body 12 into the unextended second position, which causes ears 140 to push against end walls 162 of cover 148, thereby forcing quick-release assembly 132 to move longitudinally toward proximal end 20 of tubular body 12. This causes end cap 28 and plunger 26 to retract from compressible seal 24, which substantially completely removes the compressive forces from compressible seal 24. Compressible seal 24 may thereby be placed in a released position. The compressive forces are substantially removed from compressible seal 24 regardless of how far shaft 106 and plunger 26 have been advanced into compression chamber 32 by rotating end cap 28.

FIGS. 4 and 5 show how the compressible seal 24 can be switched from being in a completely sealed position (FIG. 4) to a substantially unsealed position (FIG. 5) by simply pressing quick-release lever 130 toward the tubular body 12 of valve apparatus 10. The compressible seal 24 can likewise be returned to the completely sealed position as in FIG. 4 by simply rotating quick-release lever 130 away from tubular body 12. An important feature of quick-release mechanism 128 is that when compressible seal 24 moves from the compressible position to the released position and then back to the compressible position, compressible seal 24 will have substantially the same compressive forces acting thereon as before quick-release mechanism 128 was activated. This results in substantially the same level of constriction or sealing being maintained. Hence, the quick-release mechanism 128 allows for release and resealing of the seal 24 while maintaining substantially the same adjustment to the seal 24 caused by previous rotation of rotatable end cap 28.

For example, if compressible seal 24 had sufficient compressive force acting thereon to form a seal about itself as in FIG. 4, or about an elongated instrument 64 as in FIG. 7, but is then moved to the released position by activating quick-release mechanism 128, upon quick-release mechanism 128 being moved back to the inactivated position, compressible seal 24 will return to the same position with the same degree of sealing before it was moved. This allows a user to quickly release the seal 24 and make adjustments to, or even insert a new, elongated instrument 64 within valve assembly 10 without having to make any further adjustments on the amount of compressive forces acting on compressible seal 24, assuming that the same diameter instrument 64 is used.

FIGS. 6–10 illustrate alternate embodiments of compressible seal 24 and plunger 26 that can be used with valve apparatus 10. The majority of features previously discussed apply to alternative embodiments such that they will function in substantially the same manner. The features that remain substantially unchanged are identified with the same reference numbers as used in FIGS. 1–5. Only those features that have been substantially altered will be renumbered and described in detail.

Figure 6:
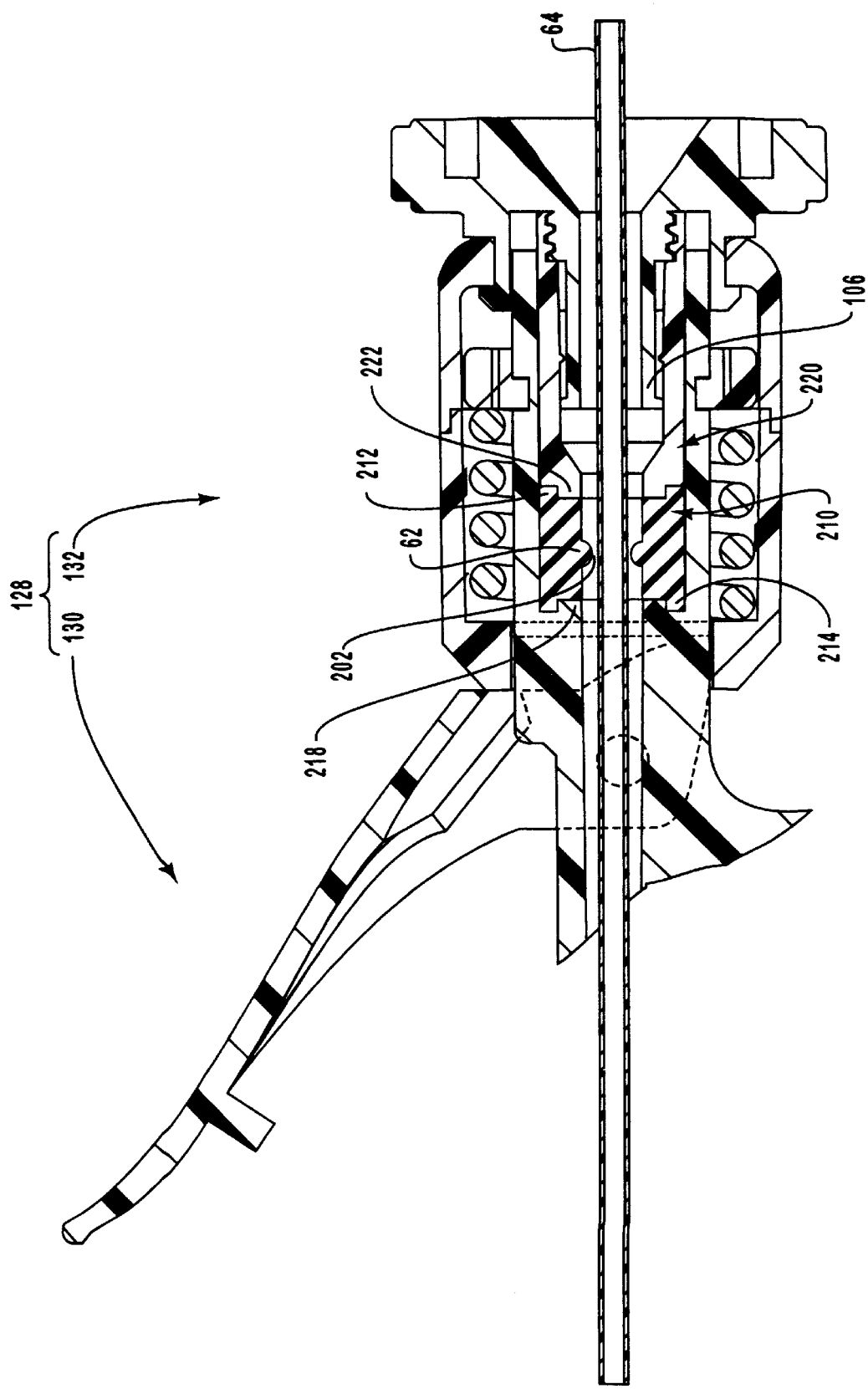
FIG. 6 is an enlarged cross-sectional view of a portion of the valve apparatus of FIG. 3 with an elongated instrument therethrough and the quick-release mechanism in the inactivated position, but with an alternate embodiment of the compressible seal.

FIG. 6 depicts an alternative compressible seal 210 that can be used in place of compressible seal 24. Alternate compressible seal 210 comprises an exterior surface 62 and interior surface 58 extending between a proximal end 54 and a distal end 56. Alternate compressible seal 210 has a substantially cylindrical configuration. Unlike compressible seal 24, alternate compressible seal 210 does not have a tapered distal end 56.

Instead, alternate compressible seal 210 has an annular distal tongue 214 extending distally from distal end 56. Correspondingly, alternate distal end 36 of compression chamber 32 has an annular ridge 218 encircling proximal end 44 of lumen 30 projecting proximally into distal end of compression chamber 32. The outside diameter of annular ridge 218 defines an annular receiving groove (not numbered) configured and sized to receive annular distal tongue 214 therein. The inside diameter of annular distal tongue 214 is substantially the same as the outside diameter of annular ridge 218. As depicted in FIG. 6, distal tongue 214, annular ridge 218, and the annular receiving groove (not numbered) are substantially rectangular in cross-section. Various other configurations may be equally effective in carrying out the intended function thereof as long as distal tongue 214, annular ridge 218, and the annular receiving groove (not numbered) are similarly sized and configured so as to cooperate together in a sealing fashion.

Proximal end 56 of alternate compressible seal 210 has an annular proximal tongue 212 extending proximally therefrom. The interior surface of annular proximal tongue 212 has a diameter that is larger than the diameter of passageway 60 defined by interior surface 58 of alternate compressible seal 210. Correspondingly, distal end 70 of alternate plunger 220 has an annular ridge 222 projecting distally therefrom. The diameter of outside surface of annular ridge 222 is substantially the same as the inside diameter of annular proximal tongue 212 and encircles the opening defined by force transferring portion 84 of plunger 220. The outside diameter of annular ridge 222 defines an annular recess (not numbered) configured to receive proximal tongue 212 therein.

Proximal tongue 212 is disposed in the annular recess defined by annular ridge 222. Annular proximal tongue 212 and annular ridge 222 are depicted in FIG. 6 as being substantially rectangular in cross-section. Other configurations may be equally effective in carrying out the intended function thereof. Proximal tongue 212 and annular ridge 222 should be similarly sized and configured so as to cooperate in a sealing fashion.

One advantage of this alternate embodiment is that the annular receiving groove defined by annular ridge 218 retains annular distal tongue 214 therein, thereby preventing distal end 56 of alternate compressible seal 210 from sliding into lumen 30 of tubular body 12 as the compressive force exerted on compressible seal 24 is increased. Similarly, the annular recess defined by annular ridge 222 projecting from distal end 70 of alternate plunger 220 holds proximal tongue 212 in place and prevents proximal end 54 of compressible seal 210 from sliding into passageway 60 as plunger 220 exerts increased compressive force on compressible seal 210.

Figure 8:
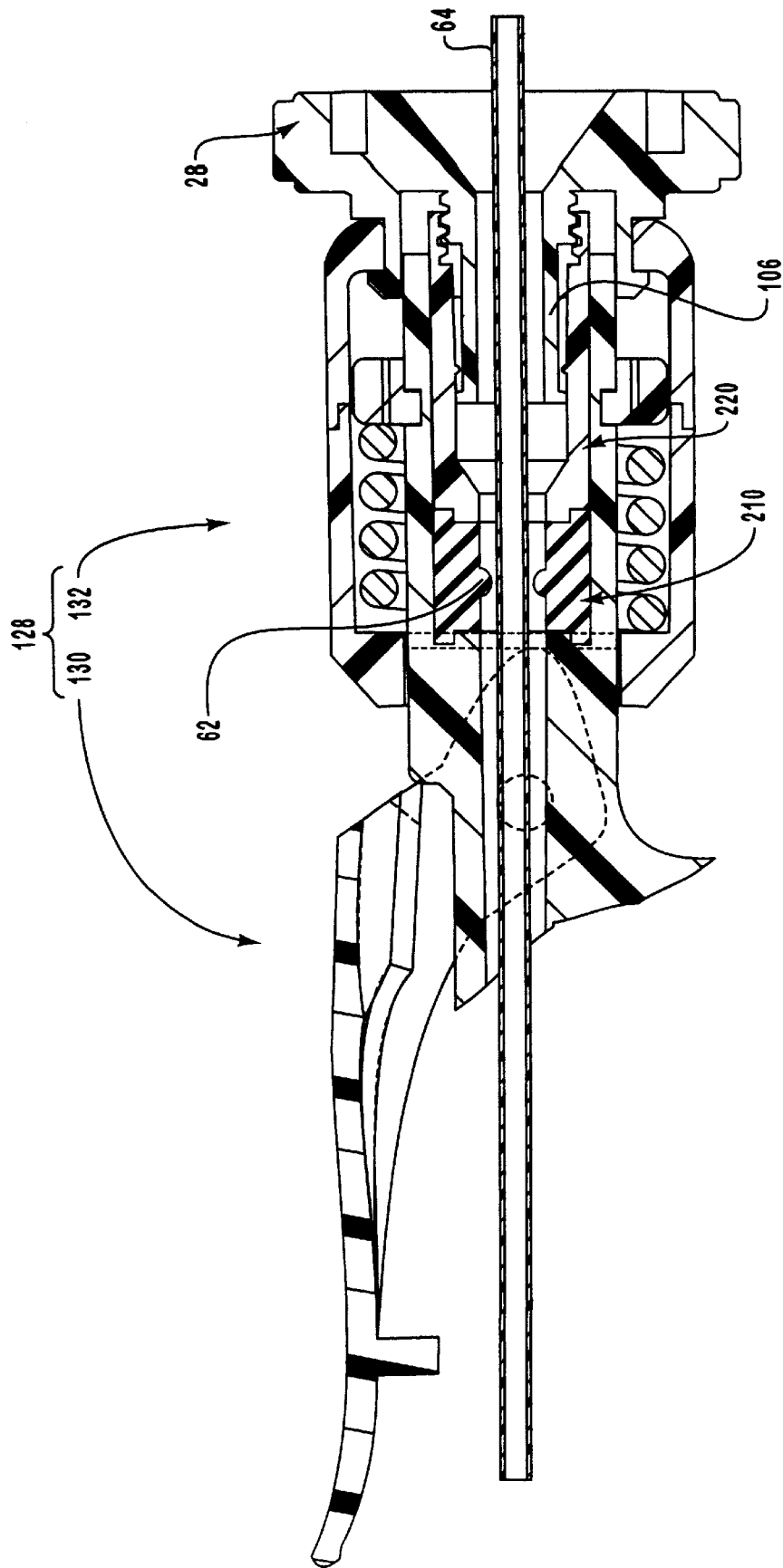
FIG. 8 is an enlarged cross-sectional view of the valve apparatus/elongated instrument combination of FIG. 7 with the quick-release mechanism in the activated position so that the compressible seal is moved into an uncompressed, unsealed position.

FIGS. 6–8 depict the same movement of quick-release mechanism 128 as shown in FIGS. 3–6, but with a medical device such as an elongated instrument 64 disposed therein. In FIG. 6, quick-release mechanism 128 is in the inactivated position, which allows compressible seal 210 to be a compressed by rotating end cap 28. As depicted in FIG. 6, end cap 28 has not yet been rotated to advance plunger 220 in order to exert a compressive force onto compressible seal 210. When alternate compressible seal 210, or compressible seal 24 (FIG. 5), are in a completely uncompressed condition, a slight gap 202 will generally exist between raised annular rib 62 and elongated instrument 64, as depicted in FIG. 6. However, gap 202 is sufficiently small such that even when compressible seal 210 is substantially uncompressed, raised annular rib 62 will be able to block a substantial quantity of fluids that may pass into passageway 60.

In order to form a complete seal around instrument 64, end cap 28 may be rotated slightly to cause alternate plunger 220, or plunger 26 (FIG. 3), to exert a compressive force on compressible seal 210. As shown in FIG. 7, end cap 28 may be selectively rotated to advance plunger 220 to exert compressive forces upon compressible seal 210 and cause raised annular rib 62 and interior surface 58 of compressible seal 24 to move radially inward in an amount sufficient to close gap 202 and to form a seal about elongated instrument 64. In a preferred condition, raised annular rib 62 will exert very little radial force against elongated instrument 64 while nevertheless maintaining an adequate seal. This allows for longitudinal adjustments or removal of elongated instrument 64 to be made without the user having to rotate end cap 28 to release substantially all the compressive force acting on compressible seal 210 every time elongated instrument 64 is to be moved.

Raised annular rib 62 of compressible seal 210 is configured to incrementally adjust the tightness of the seal around elongated instrument 64 in precise increments when end cap 28 is rotated. The user of valve assembly 16 or 216 is able to selectively advance rotatable end cap 28 to precisely adjust the tightness of the seal formed around elongated instrument 64 as desired. The tightness of the seal around elongated instrument 64 is directly related to the amount of force exerted by raised annular rib 62 on elongated instrument 64. The ability of annular rib 24 to compress provides a "sealing window" where compressible seal 210 remains sealed around elongated instrument 64 to varying degrees by exerting varying amounts of force on elongated instrument 64. Compressing annular rib 62 less tightly allows elongated instrument 64 to be repositioned or even removed without removing the seal around instrument 64.

Moreover, compressible seal 210 is preferably configured so that when it is compressed causing raised annular rib 62 to bulge radially inward and to contact elongated instrument 64, a seal is quickly formed although only a minor compressive force may be applied initially. Continued advancement of end cap 28 increases the compressive force acting on compressible seal 210 and, consequently, the force acting on elongated instrument 64 by raised annular rib 62. The amount of compressive forces acting on the elongated instrument 64 may be selectively controlled by rotating end cap 28 and is often referred to in industry as the "drag" acting on elongated instrument 64. Advantageously, the user of valve apparatus 10 can minimize the drag acting on elongated instrument 64 if desired when repositioning or moving elongated instruments 64 while still maintaining an adequate seal about elongated instrument 64. As such, elongated member 64 can be repositioned or even removed while maintaining a seal sufficient to substantially minimize the loss of body fluid from valve assembly 16 or 216.

As depicted in FIG. 8, quick-release mechanism 128 may be activated, which causes compressible seal 210 to move into the released position. When compressible seal 210 is in the released position, there are substantially no compressive forces acting thereon. Because quick-release mechanism 128 cases quick-release assembly 132 to move in a direction opposite to the direction of plungers 26 or 220 as the compressible seals 24 or 210 are compressed, and to a greater magnitude that what is possible by rotating end cap 28, no significant compressive forces will be exerted on compressible seal 24 even if end cap 28 is rotated into the most compressed position. Accordingly, rotating end cap 28 while quick-release mechanism 128 is in the activated position will generally not move the compressive seal out of a released and substantially unsealed position, in the embodiments depicted in FIGS. 1–8.

Although the discussion of FIGS. 6–8 addressed compressible seal 210, plunger 220, and valve assembly 216, it is intended to apply equally to all other disclosed embodiments, such as those of FIGS. 1–5.

Figure 9:
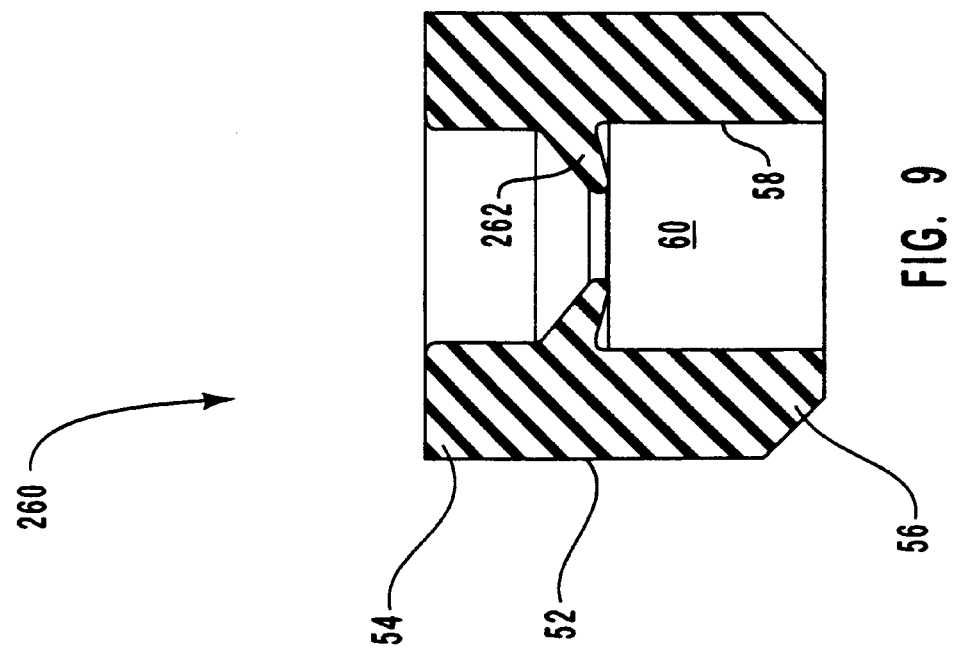
FIG. 9 is an enlarged cross-sectional view of an alternate embodiment of a compressible seal for use in combination with the valve apparatus of the present invention.

FIG. 9 illustrates another alternate compressible seal 260 that can be used in place of compressible seal 24. Alternate compressible seal 260 comprises exterior surface 52 and interior surface 58 extending between proximal end 54 and distal end 56. Alternate compressible seal 260 has a substantially cylindrical configuration with a tapered distal end 56 that is configured to cooperate with tapered shoulder 42 in compression chamber 32 (FIG. 2). Alternate compressible seal 260 also comprises a raised annular portion such as, by way of example and not by limitation, an annular fin 262 that is integrally formed on interior surface 58 and which extends into passageway 60. Alternate compressible seal 260 is compressed in the same manner as compressible seal 24 illustrated in FIGS. 1–8, thus causing annular fin 262 and interior surface 58 to move radially inward to form a seal in response to the compressive force exerted onto plunger 26 by rotating end cap 28.

Figure 10:
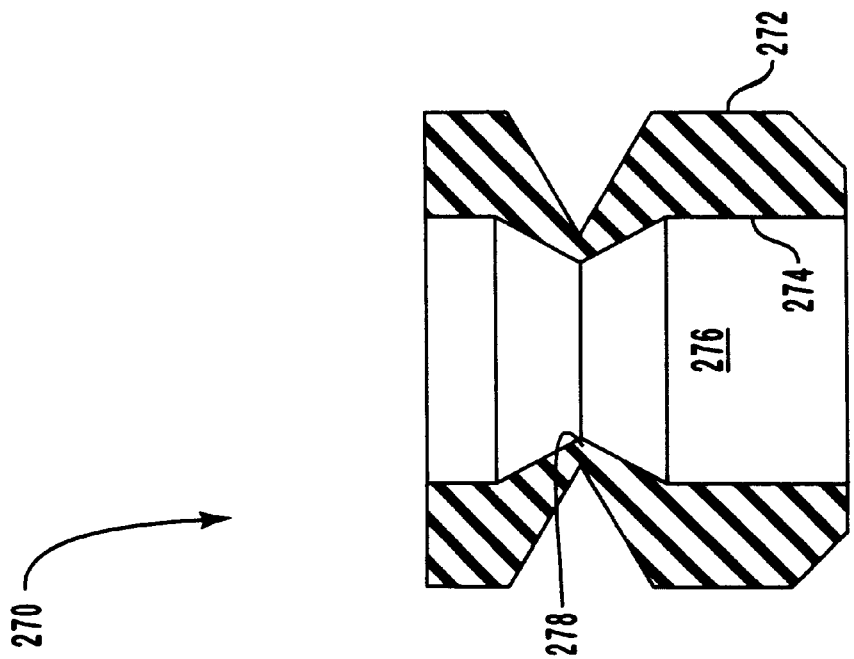
FIG. 10 is an enlarged cross-sectional view of an alternate embodiment of a compressible seal for use in combination with the valve apparatus of the present invention.

FIG. 10 illustrates an alternate compressible seal 270 that can be used in place of compressible seal 24. Alternate compressible seal 270 has exterior surface 272 and interior surface 274 extending between proximal end 54 and distal end 56. Interior surface 274 has a substantially hour-glass-shape and defines a passageway 276 that extends longitudinally through alternate compressible seal 270 and is axially aligned with lumen 30 in tubular body 12. The hour-glass shape of interior surface 274 of alternate compressible seal 270 creates a raised annular portion such as, by way of example and not limitation, central peak 278 at the narrowest portion of passageway 276 of alternate compressible seal 270. Exterior surface 272, as illustrated, is also substantially hour-glass shaped. It could, however, be substantially cylindrical without affecting the function thereof. When a compressive force is exerted upon compressible seal 270, center peak 278 moves radially inward to form a seal either against itself or about elongated instrument 64 when elongated instrument 64 is inserted through passageway 276.

The present invention may be embodied in other specific forms without departing from its spirit or essential characteristics. The described embodiments are to be considered in all respects only as illustrated and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A valve apparatus comprising:
   (a) body means for providing a lumen therethrough and which is adapted for accessing the cardiovascular or other intravenous system of a patient;
   (b) sealing means, disposed in said body means, for selectively sealing and unsealing said lumen in response to a compressive force acting on said sealing means, said sealing means including a longitudinal passageway therethrough which communicates with said lumen and provides access thereto, said sealing means responding to changes in said compressive force so as to selectively seal and unseal said passageway;
   (c) compressing means communicating with said sealing means for applying a desired amount of compressive force on said sealing means; and
   (d) quick-release means, communicating with said compressing means, for selectively releasing and restoring the desired amount of compressive force applied by said compressing means on said sealing means.

2. A valve apparatus as defined in claim 1, wherein said compressing means allows for selectively applying a varying amount of compressive force on said sealing means.

3. A valve apparatus as defined in claim 2, wherein said quick-release means comprises a quick-release mechanism movably attached to said body means and configured to selectively move between an inactivated position, wherein said compressing means may selectively apply a desired amount of compressing force on said sealing means, and an activated position, wherein said desired amount of compressing force is substantially released.

4. A valve apparatus as defined in claim 1, further comprising biasing means communicating with said compressing means for urging said compressing means into a position that allows for application of the desired compressive force on said sealing means.

5. A valve apparatus as defined in claim 4, wherein said quick-release means is able to selectively oppose said biasing means and move said compressing means into a position that substantially releases at least a portion of the compressive force applied by said compressing means on said sealing means.

6. A valve apparatus as defined in claim 4, wherein said biasing means urges said quick-release means into an inactivated position wherein said compressing means may apply the desired amount of compressing force on said sealing means.

7. A valve apparatus as defined in claim 4, wherein said biasing means comprises a spring.

8. A valve apparatus as defined in claim 1, wherein said quick-release means comprises a quick-release mechanism including:
   (a) a lever selectively movable between an extended position, wherein said quick-release mechanism is in an inactivated position so that said compressing means is able to apply the desired amount of compressive force on said sealing means, and an unextended position, wherein said quick-release mechanism is in an activated position so that the desired amount of compressive force on said sealing means is substantially released; and
   (b) a quick-release assembly operably connected to said lever and communicating with said compressing means to selectively release and restore the desired amount of compressive force, said quick-release assembly moving in response to said lever being selectively moved between said extended position and said unextended position.

9. A valve apparatus as defined in claim 1, wherein said compressing means are substantially nonadjustable.

10. A valve apparatus as defined in claim 1, wherein said compressing means comprises:
    (a) shaft means for applying compressive force on said sealing means; and
    (b) coupling means for selectively varying the amount of compressive force applied by said shaft means on said sealing means.

11. A valve apparatus as defined in claim 10, wherein said compressing means comprises:
    (a) a rotatable end cap;
    (b) a plunger movably attached to said shaft by said coupling means, said plunger extending into said compression chamber and contacting a proximal end of said sealing means, wherein said plunger increases the compressive force on said sealing means when the end cap is rotated one direction relative to said body means and wherein said plunger decreases the compressive force on said sealing means when the end cap is rotated in an opposite direction relative to said body means.

12. A valve apparatus as defined in claim 11, wherein said coupling means comprises:
    (a) first engagement threads disposed on a surface of said plunger; and
    (b) second engagement threads positioned on a surface of said end cap, said second engagement threads being configured for threaded engagement with said first engagement threads.

13. A valve apparatus as defined in claim 1, wherein said body means includes a compression chamber, wherein said sealing means comprises a compressible seal disposed within said compression chamber, wherein said seal has a shape configured to form a seal between an outer surface of said seal and a corresponding inner surface of said compression chamber.

14. A valve apparatus as defined in claim 1, wherein said sealing means comprises a compressible seal having an interior surface defining said longitudinal passageway and having a raised annular portion projecting into said passageway.

15. A valve apparatus as defined in claim 14, wherein said raised annular portion formed in said passageway of said compressible seal is capable of forming a desired seal around an instrument disposed therein sufficient to substantially prevent body fluids that may be present inside said lumen from passing through said passageway while allowing for longitudinal movement and adjustment of said instrument.

16. A valve apparatus as defined in claim 15, wherein said raised annular portion is sufficiently flexible and resilient in order that said compressible seal is able to provide a sealing window wherein the compressive force applied to the compressible seal may be significantly altered while maintaining the desired seal around said instrument.

17. A valve apparatus as defined in claim 14, wherein said raised annular portion comprises an annular rib.

18. A valve apparatus as defined in claim 14, wherein said raised annular portion comprises a fin.

19. A valve apparatus as defined in claim 14, wherein said compressible seal has an outer surface that is substantially cylindrical-shaped.

20. A valve apparatus as defined in claim 14, wherein said compressible seal has a substantially hour-glass shape configuration when in a substantially uncompressed state.

21. A valve apparatus comprising:
    (a) body means for providing a lumen therethrough and which is adapted for accessing the cardiovascular or other intravenous system of a patient, said body means including a compression chamber;
    (b) a resiliently deformable compressible seal disposed within said compression chamber and configured to selectively seal and unseal said lumen in response to a compressive force applied to said compressible seal, said compressible seal including an interior surface defining a longitudinal passageway through said seal which communicates with said lumen and provides access thereto, said interior surface having a raised annular portion projecting into said passageway, said compressible seal assuming a normally unsealed condition when not subjected to a compressive force, said compressible seal responding to changes in said compressive force so as to selectively seal and unseal said passageway;
    (c) adjustable compressing means for selectively applying a varying amount of compressive force on said compressible seal, said compressing means being adjustable to a desired compression adjustment in order to apply a desired amount of compressive force on said compressible seal;
    (d) biasing means, communicating with said compressing means, for urging said compressing means into a position that allows for application of the desired amount of compressive force on said compressible seal; and
    (e) quick-release means, movably attached to said body means and communicating with said compressing means, for selectively opposing said biasing means in order to selectively release and restore the desired amount of compressive force applied by said compressing means on said compressible seal, wherein the desired amount of compressive force is substantially released when said quick-release means is moved from a deactivated position to an activated position in opposition to said biasing means and wherein said compressing means is substantially restored to the desired compression adjustment when said quick-release means is returned to said deactivated position.

22. A valve apparatus as defined in claim 21, wherein said compressing means comprises:

(a) shaft means for applying compressive force on said sealing means; and (b) coupling means for selectively varying the amount of compressive force applied by said shaft means on said sealing means.

23. A valve apparatus as defined in claim 21, wherein said quick-release means comprises a quick-release mechanism including:

(a) a lever selectively movable between an extended position, wherein said quick-release mechanism is in said deactivated position so that said compressing means is able to apply the desired amount of compressive force on said sealing means, and an unextended position, wherein said quick-release mechanism is in said activated position so that the desired amount of compressive force on said sealing means is substantially released; and (b) a quick-release assembly operably connected to said lever and communicating with said compressing means to selectively release and restore the desired amount of compressive force, said quick-release assembly moving in response to said lever being selectively moved between said extended position and said unextended position.

24. A valve apparatus comprising:

(a) an elongated tubular body having a lumen formed therethrough and adapted for accessing the cardiovascular or other intravenous system of a patient, said tubular body including a compression chamber which communicates with said lumen;

(b) a resiliently compressible seal disposed within said compression chamber, said seal including an interior surface which defines a longitudinal passageway and a raised annular portion projecting from said interior surface into said passageway, wherein said passageway is aligned with said lumen and provides access thereto, said compressible seal being configured to assume a normally unsealed condition when not subjected to any compressive force, said compressible seal responding to changes in said compressive force so as to selectively seal and unseal said passageway;

(c) adjustable compressing means, communicating with said compressible seal, for selectively applying a desired amount of compressive force on said seal, said compressing means increasing said compressive force on said compressible seal when said compressing means is rotated in one direction relative to said body means, and said compressing means decreasing said compressive force on said compressible seal when said compressing means is rotated in an opposite direction relative to said body means;

(d) biasing means, communicating between said tubular body and said compressing means, for urging said compressing means into a position that allows for said selective application of the desired amount of compressive force by said compressing means on said compressible seal;

(e) a quick-release mechanism movably attached to said tubular body and communicating with said compressing means for selectively opposing said biasing means in order to selectively release and restore the desired amount of compressive force applied by said compressing means on said compressible seal, wherein the desired amount of compressive force is substantially released when said quick-release mechanism is moved from a deactivated position to an activated position in opposition to said biasing means and wherein said compressing means is substantially restored to the desired compression adjustment when said quick-release mechanism is returned to said deactivated position, said quick-release mechanism further comprising:

(i) a lever rotatably attached to said tubular body; and (ii) a quick-release assembly operably connected to said lever and communicating with said compressing means for selectively releasing and then restoring the desired amount of compressive force applied by said compressing means on said compressible seal.

25. A valve apparatus as defined in claim 24, wherein said compressing means includes a rotatable end cap and a plunger movably connected to said end cap by a coupling means for selectively advancing and retracting said plunger within said compression chamber, wherein said plunger engages said compressible seal in order to apply the desired compressive force.

26. A valve apparatus as defined in claim 25, wherein said coupling means comprises:

(a) first engagement threads disposed on a surface of said plunger; and (b) second engagement threads positioned on a surface of said end cap, said second engagement threads being configured for threaded engagement with said first engagement threads.

27. A valve apparatus comprising:

(a) a generally tubular body having a lumen formed therethrough adapted for accessing the cardiovascular or other intravenous system of a patient, said tubular body including a hollow compression chamber therewithin communicating with said lumen;

(b) a resilient compressible seal disposed within said compression chamber, said seal including an interior surface which defines a longitudinal passageway and a raised annular portion projecting from said interior surface into said passageway, wherein said passageway is aligned with said lumen and provides access thereto, said compressible seal being configured to assume a normally unsealed condition when not subjected to any compressive force, said compressible seal responding to changes in said compressive force so as to selectively seal and unseal said passageway;

(c) a quick-release lever hingedly attached to said tubular body and movable relative thereto;

(d) a quick-release assembly movably attached to said tubular body and operably connected to said quick-release lever, wherein said lever can be selectively moved relative to said tubular body in order to selectively move said quick-release assembly between an inactivated position, wherein said compressible seal may be subjected to a desired compressive force, and an activated position, wherein at least a substantial portion of the compressive force is released from said compressible seal;

(e) biasing means, communicating between said tubular body and said quick-release assembly, for urging said quick-release assembly into said inactivated position such that said compressible seal may be subjected to the desired compressive force, wherein said quick-release lever opposes said biasing means when moving said quick-release assembly into said activated position;

(f) an end cap rotatably connected to said quick-release assembly; and (g) a plunger operably connected to said end cap and communicating with said compressible seal within said compression chamber such that rotation of said end cap relative to said tubular body causes said plunger to selectively increase and decrease the compressive force applied to said compressible seal in order to apply the desired compressive force to said compressible seal.

28. A valve apparatus as defined in claim 27, wherein said plunger is movably connected to said end cap by a coupling means for advancing said plunger into said compression chamber.

29. A valve apparatus as defined in claim 28, wherein said coupling means comprises:

(a) first engagement threads disposed on a surface of said plunger; and (b) second engagement threads positioned on a surface of said end cap, said second engagement threads being configured for threaded engagement with said first engagement threads.

30. A valve apparatus as defined in claim 27, wherein said quick-release assembly is moved into said activated position in opposition to said biasing means when said quick-release lever is hingedly moved away from said tubular body, and wherein said quick-release assembly is moved into said inactivated position in response to said biasing means when said quick-release lever is hingedly moved toward said tubular body.

31. A valve apparatus as defined in claim 27, wherein said quick-release assembly comprises a casing assembly movably disposed around said tubular body, said casing assembly having a spaced apart relationship with an exterior surface of said tubular body in order to define a gap therebetween.

32. A valve apparatus as defined in claim 31, wherein said biasing means comprises a spring disposed within said gap between said casing assembly and said tubular body.

33. A valve apparatus as defined in claim 31, wherein said casing assembly further includes:

(a) a cover movably mounted around said tubular body and configured and oriented such that said cover operably communicates with said quick-release lever; and (b) a housing connected to and axially aligned with said cover and having an aperture formed at an end distal to said cover for receiving said end cap in a rotatable connection.

* * * * *

UNITED STATES PATENT AND TRADEMARK OFFICE
CERTIFICATE OF CORRECTION

PATENT NO. : 5,921,968
DATED : July 13, 1999
INVENTOR(S) : Fred P. Lampropoulos, Brian W. Stevens It is certified that error appears in the above-identified patent and that said Letters Patent is hereby corrected as shown below:

Col. 2, ln. 49: after "force" change "take" to --takes--

Col. 3, ln. 65: after "guidewire" and before "be" insert --to--

Col. 12, ln. 45: after "slightly larger" change "that" to --than--

Col. 14, ln. 21: after "130" change "SO" to --so--

Col 14, ln. 43: before "recesses" change "comprises" to --comprise--

Col. 16, ln. 15: after "shown" change "is" to --in--

Col. 18, ln. 30: before "compression" delete [11]

Col. 18, ln. 55: before "rotated" delete [been]

Col. 20, ln. 36: after "to be" delete [a]
Col. 21, ln. 39: after "128" change "cases" to --causes--
Col. 22, ln. 26: after "only as" change "illustrated" to --illustrative--

Signed and Sealed this

Fourth Day of July, 2000

Attest:

Q. TODD DICKINSON

Attesting Officer          Director of Patents and Trademarks